(12) United States Patent
Littleford

(10) Patent No.: US 8,084,652 B2
(45) Date of Patent: Dec. 27, 2011

(54) CONVERTING $CO_2$ TO AN ALCOHOL

(75) Inventor: Wayne S. Littleford, Griffith (CA)

(73) Assignee: Eco Power Solutions (USA) Corp., Quincy, MA (US)

( * ) Notice: Subject to any disclaimer, the term of this patent is extended or adjusted under 35 U.S.C. 154(b) by 0 days.

(21) Appl. No.: 12/882,693

(22) Filed: Sep. 15, 2010

(65) Prior Publication Data

US 2011/0067411 A1 Mar. 24, 2011

Related U.S. Application Data

(60) Provisional application No. 61/243,836, filed on Sep. 18, 2009.

(51) Int. Cl.
*C07C 29/12* (2006.01)
(52) U.S. Cl. ........ 568/888; 568/300; 568/700; 568/840; 568/884; 568/890
(58) Field of Classification Search .......................... None
See application file for complete search history.

(56) References Cited

U.S. PATENT DOCUMENTS

| | | | |
|---|---|---|---|
| 3,095,458 A * | 6/1963 | Pirkle et al. | 568/890 |
| 4,761,505 A * | 8/1988 | Diana et al. | 568/918 |
| 5,321,946 A | 6/1994 | Abdelmalek | |
| 6,344,177 B1 * | 2/2002 | Littleford | 423/210 |
| 6,508,915 B1 | 1/2003 | Osuda et al. | |
| 2006/0204407 A1 * | 9/2006 | McWhorter | 422/168 |

FOREIGN PATENT DOCUMENTS

| | | | |
|---|---|---|---|
| GB | 2461723 A | | 1/2010 |
| KR | 2005017649 A | * | 2/2005 |
| WO | 9530113 A1 | | 11/1995 |

OTHER PUBLICATIONS

Winnicka et al, J.of Radioanalytical and Nuclear Chemistry, 2009, vol. 280, No. 1, pp. 79-84.*

* cited by examiner

*Primary Examiner* — Sudhakar Katakam
(74) *Attorney, Agent, or Firm* — Osha • Liang LLP

(57) ABSTRACT

In general, in one aspect, the invention relates to a method to convert carbon dioxide ($CO_2$) to an alcohol. The method involves contacting a stream of flue gas comprising the $CO_2$ from a combustion process with water mist to create a mixture of liquid carbonic acid ($H_2CO_3$) and wastewater. The method further involves extracting the liquid $H_2CO_3$ from the mixture and pressurizing the liquid $H_2CO_3$ to generate pressurized liquid $H_2CO_3$. The method further involves combining the pressurized liquid $H_2CO_3$ with a first liquid reagent in a first hydrolysis chamber creating the alcohol from combining the pressurized liquid $H_2CO_3$ with the first liquid reagent.

8 Claims, 6 Drawing Sheets

CONVERTING $CO_2$ TO AN ALCOHOL

CROSS-REFERENCE TO RELATED APPLICATIONS

This application claims priority pursuant to 35 U.S.C. §119(e) to U.S. Provisional Patent Application No. 61/243,836 entitled "Converting CO2 to Alternative Fuel," filed Sep. 18, 2009 in the name of Wayne S. Littleford, the disclosure of which is incorporated by reference herein in its entirety.

BACKGROUND

Controlling and reducing carbon dioxide ($CO_2$) is a growing environmental concern. The release of $CO_2$ into the atmosphere is believed by some experts to contribute to a phenomenon known as "global warming" or the "greenhouse effect," where the $CO_2$ creates an insulating effect in the Earth's atmosphere, reflecting some of the sun's solar radiation back to Earth and slowly raising the global temperature. As the global temperature rises, some experts believe that the Earth's environment may undergo dynamic and potentially catastrophic changes. Consequently, national and local governments throughout the world, including within the United States, have enacted legislation and/or regulations to control the production and/or consumption of $CO_2$. Further, many companies and individuals are taking steps to reduce their own "carbon footprint" on a voluntary basis.

$CO_2$ originates from a variety of sources, many of which involve the combustion of an organic fuel such as coal, natural gas, gasoline, fuel oil, and methane. Specifically, combustion processes that are used for the generation of electricity and/or heat are a significant source of $CO_2$. Many of these combustion processes require and/or have a form of emission control capability. Such emission control capability may reduce one or more pollutants created by the combustion process. Some of the pollutants that are sought to be controlled include, but are not limited to, carbon dioxide, sulfur dioxide, nitrogen oxide, and mercury.

SUMMARY

In general, in one aspect, the invention relates to a method to convert carbon dioxide ($CO_2$) to an alcohol. The method involves contacting a stream of flue gas comprising the $CO_2$ from a combustion process with water mist to create a mixture of liquid carbonic acid ($H_2CO_3$) and wastewater. The method further involves extracting the liquid $H_2CO_3$ from the mixture and pressurizing the liquid $H_2CO_3$ to generate pressurized liquid $H_2CO_3$. The method further involves combining the pressurized liquid $H_2CO_3$ with a first liquid reagent in a first hydrolysis chamber creating the alcohol from combining the pressurized liquid $H_2CO_3$ with the first liquid reagent.

In general, in one aspect, the invention relates to a system for converting carbon dioxide ($CO_2$) to an alcohol. The system includes a receiving system comprising a pressurized water misting array and configured to contact a stream of flue gas comprising $CO_2$ from a combustion process with water mist to create a mixture of liquid carbonic acid ($H_2CO_3$) and wastewater. The system further includes an acid separation system configured to separate the liquid $H_2CO_3$ from the mixture and purify the liquid $H_2CO_3$ to create purified liquid $H_2CO_3$. The system further includes an acid conversion system comprising a plurality of fogging pumps, a reagent storage tank, and a plurality of hydrolysis chambers. The acid conversion system is configured to pressurize the purified liquid $H_2CO_3$ using a first of the plurality of fogging pumps to create pressurized liquid $H_2CO_3$ and combine the pressurized liquid $H_2CO_3$ with a first liquid reagent, extracted from the reagent storage tank, in a first of the plurality of hydrolysis chambers. The acid conversion system is further configured to create a first primary alcohol from combining the pressurized liquid $H_2CO_3$ with the first liquid reagent.

DETAILED DESCRIPTION

Figure 1:
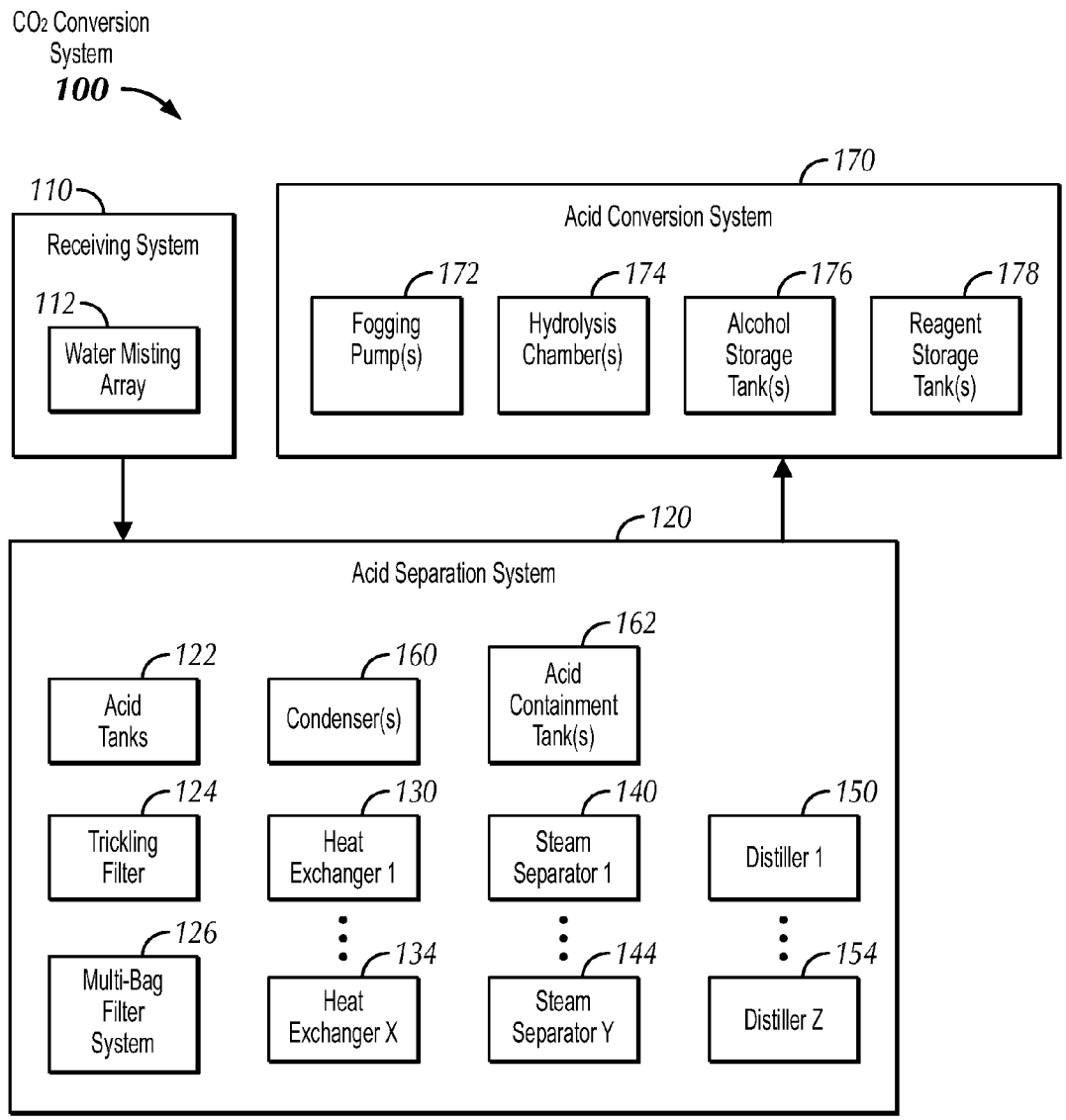
FIG. 1 shows a system in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide for converting $CO_2$ to an alcohol. More specifically, one or more embodiments of the invention provide for creating carbonic acid ($H_2CO_3$) from a stream of $CO_2$ and combining the $H_2CO_3$ with a reagent to create alcohol. The invention may further provide for creating other acids, including but not limited to sulfuric acid ($H_2SO_4$) and nitric acid ($HNO_3$) from the stream of $CO_2$ and combining those other acids with one or more reagents to create one or more alcohols. All the piping and associated fittings, pumps, valves, and other equipment are made of materials resistant to the chemicals transported, transformed, pressurized, created, or otherwise handled within those materials. As used herein, and "acid" or "acids" may refer to carbonic acid, sulfuric acid, and/or nitric acid.

Embodiments of this invention may be used in processing and manufacturing for a number of market sectors, including but not limited to food processing and packaging, pulp and paper, printing, chemicals and allied products, rubber, plastics, hospitals, universities, metal industries, drug manufacturing, wastewater and sewage treatment, beverages, utilities, incineration, steel, cosmetics, textile production, electronics, and petroleum refining.

FIG. 1 shows a $CO_2$ conversion system (100) in accordance with one or more embodiments of the invention. The $CO_2$ conversion system (100) includes a receiving system (110), an acid separation system (120), and an acid conversion system (170). The acid separation system (120) includes acid tanks (122), a trickling filter (124), a multi-bag filter system (126), a number of heat exchangers (e.g., heat exchanger 1 (130), heat exchanger X (134)), a number of steam separators (e.g., steam separator 1 (140), steam separator Y (144)), a number of distillers (e.g., distiller 1 (150), distiller Z (154)), a condenser (160), and one or more acid containment tanks (162). The acid conversion system (170) includes one or more fogging pumps (172), one or more hydrolysis chambers (174), one or more alcohol storage tanks (176), and one or more reagent storage tanks (178). Each of these components is described with respect FIG. 1 below. One of ordinary skill in the art will appreciate that embodiments of the invention are not limited to the configuration shown in FIG. 1.

For each component shown in FIG. 1, as well as any other component implied and described but not shown in FIG. 1, may be configured to receive material from one component (i.e., an upstream component) of the $CO_2$ conversion system (100) and send material (either the same as the material received or material that has been altered in some way) to another component (i.e., a downstream component) of the $CO_2$ conversion system (100). In all cases, the material received from the upstream component may be delivered through a series of pipes, pumps, valves, and/or other devices to control factors associated with the material received such as the flow rate, temperature, and pressure of the material received as it enters the component. Further, the liquid acids may be delivered to the downstream component using a different series of pipes, pumps, valves, and/or other devices to control factors associated with the material sent such as the flow rate, temperature, and pressure of the material sent as it leaves the component.

In one or more embodiments of the invention, the receiving system (110) of the $CO_2$ conversion system (100) is configured to receive a stream of flue gas containing $CO_2$. The stream of flue gas may be derived from a combustion process using a fossil fuel, including but not limited to coal, fuel oil, natural gas, gasoline, and propane. In one or more embodiments of the invention, the stream of flue gas is created during the production of heat and/or electric power using a boiler to heat water using one or more fossil fuels. The stream of flue gas may be conditioned before being received by the receiving system (110). For example, a chemical may be added to the stream of flue gas, or the temperature of the stream of flue gas may be regulated in some way. Conditioning the stream of flue gas may be performed using a separate system designed for such a purpose. An example of a receiving system (110) for conditioning the stream of flue gas is described below with respect to FIG. 3.

Pollution abatement devices used in power generation plants and large industrial plant applications are well known for removing, for example, nitrogen oxide (NOx), sulfur oxide (SOx), hydrogen chloride (HCl), mercury (Hg), partial CO2, and particulate matter (e.g., PM2.5, PM10) from the exhaust gas streams generated by coal-fired, oil-fired, natural gas-fired, and chemical process boilers. An example of such a pollution abatement device that not only recovers heat from the exhaust gas, but also removes the contaminants, is disclosed in U.S. Pat. No. 6,344,177, incorporated herein by reference. The pollution abatement process and pollution abatement device (the "COMPLY 2000®") described in U.S. Pat. No. 6,344,177 makes use of misting technology, together with cooling and condensation coils to effect targeted pollutants' removal. (COMPLY 2000 is a registered trademark of Eco Power Solutions (USA) Corp. of Quincy, Mass.)

Specifically, with respect to the COMPLY 2000, flue gas may be received from a combustion process and may come in contact with a pressurized cloud of steam or mist, which is sprayed directly against the directional flow of the flue gas, causing a pressure differential between the two flows. The steam or mist may be produced by the steam manifold or a commonly known misting device. The contact may also increase the humidity of the flue gas to about 90% or 95% relative humidity, while at the same time maintaining a high flue gas temperature. This high RH (Relative Humidity), high temperature and pressure differential may cause the flue gas POC (product of combustion) to be absorbed into the fine water droplets (5 to 10 microns in diameter), maintaining a high temperature value while also converting the POC into a wet acid composition.

The flue gas may then come into contact with a heat reclaim (i.e., cooling) coil, where the hot flue gas water droplets exchange heat with the coolants within the cooling coil to cool down the hot moist flue gas. The flue gas may pass through the cooling coil and come into contact with a second cloud of steam or mist, in a manner similar to the first cloud of steam or mist. The mist may be produced by an array of misting devices using only cold water. The flue gas, after coming into contact with the second cloud of mist, may reach total saturation, cooling the flue gas even further. The flue gas may then come into contact with the condensing coil, causing a wet film of acid droplets to be collected on the surface of the coil. As more and more droplets are collected, a stream may form, flowing downward to the drain pan where the collected liquids are directed out of the COMPLY 2000 unit to a wastewater containment facility. The flue gas process may change, depending on the different types of removal that are to be achieved. For example, to remove $NO_X$, the sequence of events may be different than those needed to remove $SO_X$. The COMPLY 2000 is described more fully below with respect to Example 2.

In one or more embodiments of the invention, the receiving system (110) is configured to apply a water mist to a stream of flue gas (which includes $CO_2$) using a water mist array (112) to create a mixture of carbonic acid ($H_2CO_3$) and wastewater. The mixture may also include other acids, including but not limited to sulfuric acid ($H_2SO_4$) and nitric acid ($HNO_3$). Each of the acids in the mixture may be in liquid form. The water mist applied to the stream of flue gas by the water mist array (112) may be pressurized and disbursed in fine droplets. In such a case, a reaction may occur because the molecules in the water mist array (112) have the "correct" collision geometry and sufficient energy created by the high-pressure foggers directed against the flue gas flow to cause a significant differential pressure and, at the same time, a significant temperature difference between the water droplets and the flue gas. As a result, some percentage (in the case of the COMPLY 2000, at least ten percent) of the $CO_2$ in the flue gas stream may undergo the following reaction:

$$CO_2 + H_2O \rightarrow H_2CO_3 \rightarrow HCO_3 + H^+$$

In one or more embodiments of the invention, the receiving system (110) is also a heat recovery system, where the captured heat may be used for other purposes associated with the combustion process. For example, a fluid that is heated to a high temperature in the receiving system (110) may be used in a heat exchanger (described below) to raise the temperature of a different fluid used in a different process, such as the process performed by the acid separation system (120).

In one or more embodiments of the invention, the acid separation system (120) uses a number of components (described below) to separate the acids from the mixture and to purify the acids (i.e., remove contaminants) before sending the acids to the acid conversion system (170) to be converted to alcohol. For example, the acid separation system (120) may be configured to separate liquid carbonic acid from the mixture of acids and wastewater received from the receiving system (110) and purify the liquid carbonic acid to create purified liquid carbonic acid. Those skilled in the art will appreciate that purifying the acids may require the substantial removal, as opposed to the complete removal, of impurities.

In one or more embodiments of the invention, the trickling filter (124) of the acid separation system (120) is used to separate the liquid acids from the wastewater in the mixture. The trickling filter (124) may consist of a fixed bed of media, including but not limited to rocks, gravel, slag, polyurethane foam, sphagnum peat moss, and plastic. In one or more embodiments of the invention, the mixture enters the trickling filter (124) and flows downward over the fixed bed of media, causing a layer or film of microbial slime to grow. The microbial slime may cover the bed of media. Aerobic conditions may be maintained in the trickling filter (124) by agitating the environment in the trickling filter (124). The environment in the trickling filter (124) may be agitated by using, for example, splashing, diffusion, forced air, or natural convection (e.g., if the filter medium is porous).

In one or more embodiments of the invention, the removal of the liquid acids from the mixture using the trickling filter (124) involves both absorption and adsorption of organic compounds within the mixture by the layer of microbial slime. Diffusion of the mixture over the media may create dissolved air containing the oxygen that the slime layer requires for the biochemical oxidation of the organic compounds. In one or more embodiment of the invention, the biochemical oxidation releases carbon dioxide gas, water, and other oxidized end products. As the slime layer thickens, it may become more difficult for air to penetrate the slime layer, which may cause an inner anaerobic layer to be formed. The slime layer may continue to build until it eventually sloughs off, breaking off longer growth into a treated effluent as a sludge that requires subsequent removal and disposal.

The treatment of a mixture, including wastewater and acids, using a trickling filter (124) is a well-known technology in the art. The trickling filter (124) may also be described as roughing filters, intermittent filters, packed media bed filters, alternative septic systems, percolating filters, attached growth processes, and fixed film processes.

In one or more embodiments of the invention, the multi-bag filter system (126) of the acid separation system (120) purifies a substance (e.g., the liquid acid(s)) by removing oils and other particles from the substance using bags of pleated cartridges housed in a vessel. The substance may be the sludge produced by the trickling filter (124) containing the liquid acids. Other solids may be suspended solids from a industrial wastewater stream. In one or more embodiments of the invention, the multi-bag filter system (126) provides a double throughput efficiency of conventional or graded mixed media filters. Under normal operating conditions, the filters may remove up to 99% of the suspended solids and up to 99% of the insoluble hydrocarbons without the use of additional chemicals. As contaminants are captured, and flow is restricted, a vacuum pressure may build and reach a designated set point, at which pressure a regeneration cycle is automatically triggered. In the regeneration cycle, the media may be cleaned and the contaminants may be moved. Completion of the regeneration cycle may be verified by a visual inspection of the media bed using a sight glass located on the multi-bag filter system (126). In one or more embodiments of the invention, a pump directs the captured contaminants out of the multi-bag filter system (126) through a backwash port.

In one or more embodiments of the invention, one or more acid containment tanks (162) of the acid separation system (120) is used to gather and hold one or more acids during the process performed by the acid separation system (120). For example, an acid containment tank (162) may be used to receive the mixture from the multi-bag filter system (126). Further, an acid containment tank (162) may be used to receive liquid acid from the condenser (160), described below. In one or more embodiments of the invention, a single acid is received from each condenser (160) and stored in its own containment tank (162). One or more different acid containment tanks (162) may be used for a different step in the process.

In one or more embodiments of the invention, each acid containment tank (162) is made of a material resistant to the chemical it stores. Each acid containment tank (162) may also be designed to operate within the mechanical parameters (pressure and temperature, erosive & corrosive) of the application under which the chemical (i.e., acid) is to be used. Each acid containment tank (162) may be impacted by a number of factors, including but not limited to heat, cold, vacuum, pressure, and the aggressive nature (acidic/caustic) of the chemical to be stored. There are short term and long term goals associated with the engineering and specification of the correct materials for an acid containment tank (162). While economic considerations may be a factor, the design of an acid containment tank (162) and how it may impact the environment is crucial. In one or more embodiments of the invention, there is a chemical profile and information report know as a "MSDS" (Material Safety Data Sheet) which is provided by a chemical manufacturer or distributor. The MSDS may be considered a starting point for design of an acid containment tank (162). An acid containment tank (162) may be designed in conjunction with a manufacturer of a chemical to be stored in the acid containment tank (162), where the manufacturer may provide some experience regarding tank materials compatible with the chemical.

In one or more embodiments of the invention, one or more heat exchangers (e.g., heat exchanger 1 (130), heat exchanger X (134)) of the acid separation system (120) is used to heat the liquid acids to a temperature above the liquid acids' boiling points. One or more of the heat exchangers may also set a temperature less than the boiling point of water. Carbonic acid, nitric acid, and sulfuric acid each boil between 170° F. and 185° F., which is much lower than the 212° F. temperature at which water boils. In other words, each of the one or more of the heat exchangers maintain the temperature of the liquid acids flowing through it at more than 185° F. and less than 212° F. In one or more embodiments of the invention, one or more of the heat exchangers may use the heat from a fluid from a different process to heat the liquid acids.

A heat exchanger (e.g., heat exchanger 1 (130), heat exchanger X (134)) may be a device built for efficient heat transfer from one fluid to another fluid. In one or more embodiments of the invention, one of the fluids is the liquid acids, and the other fluid is water. In the heat exchanger, the two fluids are separated by a solid wall so that the two fluids do not mix. For efficiency, heat exchangers may be designed to maximize the surface area of the solid wall between the two fluids, while minimizing resistance to fluid flow through both sides of the heat exchanger. The performance of the heat exchanger may also be affected by the addition of fins or corrugations on one or both sides of the solid wall, which increases surface area and may channel fluid flow or induce turbulence. A type of heat exchanger may be a plate heat exchanger, which is composed of multiple, thin, slightly-separated plates that have very large surface areas and fluid flow passages for heat transfer.

In one or more embodiments of the invention, one or more steam separators (e.g., steam separator 1 (140), steam separator Y (144)) of the acid separation system (120) is used to separate the acids in vapor form (i.e., acid in gaseous form) from the acids that remain in liquid form. The heated acid (with temperatures above 212° F. from the heat exchanger) entering the one or more steam separators may cause flashing of the heated acids, forming a mixture of acid in a gaseous form and in a liquid form. In one or more embodiments of the invention, the steam separator is designed specifically for the efficient removal of relatively small quantities of vapor mixed with liquid using nozzles, which discharge a substance (either liquid or gas) to swirl the liquid mixture inside the vessel of the steam separator. The resultant compression, along with interior baffling of the steam separator, separates the steam (acids in gaseous form), which may rise to an upper chamber of the steam separator. From the upper chamber, the acids in gaseous form may be sent to a distiller (e.g., distiller 1 (150), distiller Z (154)). The acids that remain in liquid form may be redirected to a heat exchanger (e.g., heat exchanger 1 (130), heat exchanger X (134)). The steam separator may also be referred to as a moisture separator.

In one or more embodiments of the invention, one or more distillers (e.g., distiller 1 (150), distiller Z (154)) of the acid separation system (120) is used to separate each acid in vapor form and distill each of the different acids (e.g., $HNO_3$, $H2SO_4$, and $H_2CO_3$) individually. The acids in vapor form may be received from the steam separator. Each distiller may be one large vessel with multiple compartments, where each compartment holds one of the acids separated from the acid vapor. The distiller may also be a series of separate distillation vessels. In one or more embodiments of the invention, the distiller ensures that all water has been removed from each of the acids in vapor form while also separating any liquids and returning such liquids to an acid containment tank (162). The distiller may utilize a method of separating acids in vapor form based on differences in the volatility of each acid in a boiling liquid mixture.

Distillation using a distiller may be a unit operation, or a physical separation process, and not a chemical reaction. A common misconception is that, for a liquid mixture at a given pressure, each component of the mixture boils at the boiling point corresponding to the given pressure, and the vapors of each component will collect separately and purely. This misconception, however, fails to hold true, even in an idealized system. Idealized models of distillation are essentially governed by Raoult's law and Dalton's law, and assume that vapor-liquid equilibria are attained. Raoult's law assumes that a component contributes to the total vapor pressure of the mixture in proportion to its percentage of the mixture and its vapor pressure when pure. In other words, partial pressure equals mole fraction multiplied by vapor pressure when pure. If one component changes another component's vapor pressure, or if the volatility of a component is dependent on its percentage in the mixture, the law will fail.

Dalton's law states that the total vapor pressure is the sum of the vapor pressures of each individual component in the mixture. When a multi-component liquid is heated, the vapor pressure of each component will rise, thus causing the total vapor pressure of the liquid to rise. When the total vapor pressure reaches the pressure surrounding the liquid, boiling occurs, and the liquid turns to gas throughout the bulk of the liquid. This means that a mixture with a given composition has one boiling point at a given pressure, when the components are mutually soluble. An implication of this theory is that lighter components never cleanly "boil first". At boiling point, all volatile components boil, but for a single component, its percentage in the vapor is the same as its percentage of the total vapor pressure. Lighter components have a higher partial pressure, and so are concentrated in the vapor. However, heavier volatile components also have a (smaller) partial pressure and necessarily evaporate, even though the volatile components are less concentrated in the vapor.

Indeed, batch distillation and fractionation succeed by varying the composition of the mixture. In batch distillation, the batch evaporates, which changes the composition of the mixture. In fractionation, liquid higher in the fractionation column contains more lights and boils at lower temperatures. It is not possible to completely purify a mixture of components by distillation, as this would require each component in the mixture to have a zero partial pressure. If ultra-pure products are the goal, then further chemical separation must be applied. When a binary mixture is evaporated and another component (e.g., a salt) has essentially zero partial pressure, the process is simplified and is called evaporation in engineering.

Once each acid is distilled in a distiller (e.g., distiller 1 (150), distiller Z (154)), each acid may be sent to a common header, where the acids are recombined. From the common header, the acid mixture may be sent to a condenser (160). In one or more embodiments of the invention, no common header exists, and each acid remains separated and is sent to its own individual condenser (160). The condenser (160) may be a series of heat exchangers that convert a chemical from its gaseous state to its liquid state at a pressure below atmospheric pressure. The condenser (160), sometimes also called a water-cooled condenser, may consist of a continuous tube coil mounted inside a steel shell. In one or more embodiments of the invention, chilled water flows through the coil of the condenser (160), and the acid mixture discharges inside the steel shell to condense on the outside of the coil.

Associated with the condenser (160) may be a chiller (not shown) and a cooling tower (not shown) to ensure that sufficient cooling is supplied to the condensers so as to change the acid gases into liquid. A chiller is a machine that removes heat from a liquid via a vapor-compression cycle. A vapor compression water chiller comprises the four major components of the vapor-compression refrigeration cycle (compressor, evaporator, condenser, and some form of metering). Chilled water is pumped through a process, such as the condenser (160) described above, where the chilled water is then directed back to the chiller. Cooling towers are heat removal devices used to transfer process waste heat to the atmosphere. Cooling towers may use the evaporation of water to remove process heat and cool the working fluids to a temperature near the wet bulb air temperature. Water-cooled chillers (e.g., the chiller) may normally be more energy efficient than air-cooled chillers (e.g., the cooling tower) due to heat rejection to the apparatus (e.g., tower) and water for temperatures at or near wet-bulb air temperature. From the condenser (160), the liquid acids may be sent to an acid containment tank (162) or to one or more acid storage tanks (176) in the acid conversion system (170), depending on whether the liquid acids require further refining or not. If the acids are sent to the one or more acid storage tanks (176), then each acid may be sent from an individual condenser (160) to an individual acid storage tank (176).

In one or more embodiments of the invention, the acid conversion system (170) of the CO2 conversion system (100) converts one or more liquid acids to one or more alcohols. Specifically, the acid conversion system (170) mixes a reagent with a liquid acid, under proper conditions, to induce a chemical reaction creating an alcohol.

In one or more embodiments of the invention, one or more fogging pumps (172) of the acid conversion system (170) are used to convert the liquid acids to one or more alcohols. A single fogging pump (172) may be used for a single liquid acid. Each fogging pump (172) may receive a liquid acid from an acid containment tank (162) of the acid separation system (120) and increase the pressure of the acid to 150 pounds per square inch (psi). Once at pressure, the fogging pump (172) may send the acid to a hydrolysis chamber (174). In one or more embodiments, a control valve (not shown) is used modulate the pressure and flow of the acid between the fogging pump (172) and the hydrolysis chamber (174) to maintain an even distribution of acid in the hydrolysis chamber (174).

In one or more embodiments of the invention, one or more hydrolysis chambers (174) of the acid conversion system (170) are used to convert the liquid acids to one or more alcohols. Specifically, a liquid acid may collide with a liquid reagent in the hydrolysis chamber (174) to create an alcohol. A single hydrolysis chamber may be used for a single liquid acid. The carbonic acid may be directed evenly into an array of high pressure fogging nozzles housed in the hydrolysis chamber (174). Likewise, liquid reagent may be directed evenly into a different array of high pressure fogging nozzles housed in the hydrolysis chamber (174). In one or more embodiments of the invention, the array of high pressure fogging nozzles for the liquid acid and the array of high pressure fogging nozzles for the liquid reagent are directed against each other so that, as the pressurized fluid is released from each array, there will be a contact collision of the pressurized liquids against one another. The fine liquid droplets come in contact with one another at 150 psi, and a high bust of energy is created by the collision, causing a hydrolysis reaction. In one or more embodiments of the invention, a result of the hydrolysis reaction is alcohol droplets, which fall to the bottom of the Hydrolysis chamber and are sent to an alcohol storage tank (176).

Hydrolysis is a chemical process in which a certain molecule is split into two parts by the introduction of an additional molecule. Acid-base-catalyzed hydrolyses are known in the art. One example of acid-base-catalyzed hydrolysis is the hydrolysis of amides or esters, which occurs when the nucleophile (a nucleus-seeking agent such as water or a hydroxyl ion) attacks the carbon of the carbonyl group of the ester or amide. In an aqueous base, hydroxyl ions are better nucleophiles than dipoles, such as water. In acid, the carbonyl group becomes protonated, which leads to a much easier nucleophilic attack. The products for both hydrolyses are compounds with carboxylic acid groups.

Hydrolysis chambers are manufactured using various materials such as polypropylene, Inconel® A686, Hastelloy® C276, or other precious metals. (Inconel is a registered trademark of Huntington Alloys Corporation of Huntington, W. Va. Hastelloy is a registered trademark of Haynes International, Inc., of Kokomo, Ind.) As described above, housed in the hydrolysis chamber are two arrays of high pressure fogging nozzles. Each array may have any number of, and each nozzle may distribute a stream of fine liquid droplets of a certain size or range of sizes. Ideally, each droplet is sized to allow for a large surface area for reactions to take place. In one or more embodiments of the invention, an array has up to 10 nozzles, and the each nozzle of the array is designed to disburse liquid droplets about 10 microns in diameter. The hydrolysis chamber may also have a network of connections allowing finished liquids to be directed to holding tanks or some other process. The hydrolysis chambers may be sized and manufactured based on the specific application that arises from the facility for which it is used.

The liquid reagent used to collide with the liquid acid may be stored in one or more reagent storage tanks (178). The liquid reagent may be supplied independently of the process described herein. From the reagent storage tank (178), the liquid reagent may be directed through a high pressure pump (not shown), which is used to increase the pressure of the liquid reagent to 150 psi and send the pressurized liquid reagent through a control valve (not shown). The control valve may modulate the pressure and flow of the liquid reagent to maintain an even distribution of the liquid reagent in the hydrolysis chamber (174).

Figure 2:
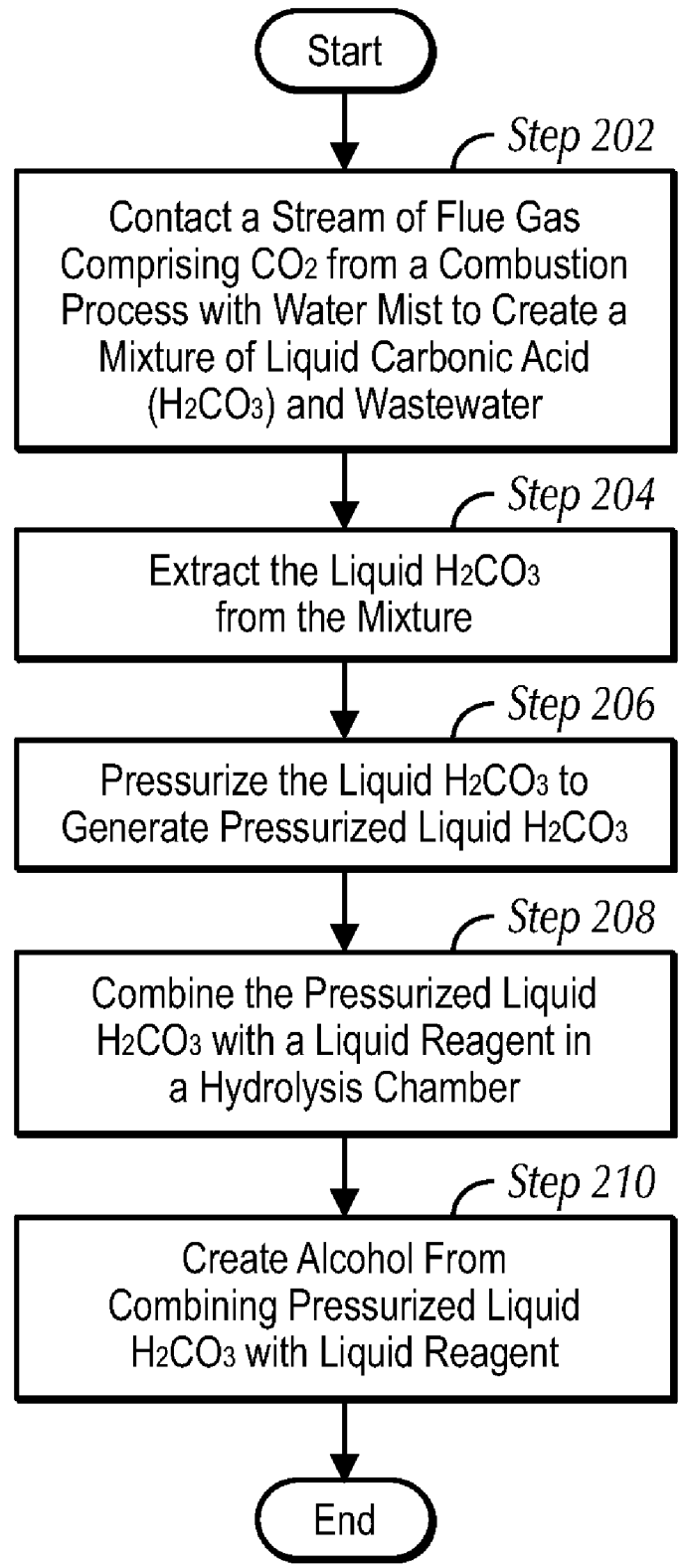
FIG. 2 shows a flowchart for a method of converting $CO_2$ to an alcohol in accordance with one or more embodiments of the invention.

FIG. 2 shows a flowchart for a method of converting $CO_2$ to an alcohol in accordance with one or more embodiments of the invention. While the various steps in this flowchart are presented and described sequentially, one of ordinary skill will appreciate that some or all of the steps may be executed in different orders, may be combined or omitted, and some or all of the steps may be executed in parallel. Further, in one or more of the embodiments of the invention, one or more of the steps described below may be omitted, repeated, and/or performed in a different order. In addition, a person of ordinary skill in the art will appreciate that additional steps, omitted in FIG. 2, may be included in performing this method. Accordingly, the specific arrangement of steps shown in FIG. 2 should not be construed as limiting the scope of the invention.

Referring to FIG. 2, in Step 202, a stream of flue gas that includes $CO_2$ and is generated during a combustion process is brought into contact with a water mist to create a mixture of carbonic acid ($H_2CO_3$) and wastewater. The mixture may also include other acids, including but not limited to sulfuric acid and nitric acid. The mixture may also include other chemicals and/or materials. In one or more embodiments of the invention, the carbonic acid and other acids are created in liquid form.

In Step 204, the liquid carbonic acid is extracted from the mixture. Other acids (e.g., sulfuric acid and nitric acid) may also be extracted from the mixture. In one or more embodiments of the invention, the carbonic acid and other acids (the "acid mix") are extracted from the mixture using a trickling filter. Specifically, the mixture with the acid mix may be received in the trickling filter having a media onto which the mixture flows under aerobic conditions. The mixture flowing over the media under aerobic conditions may result in a layer of microbial film to form on the media. Further, using the layer of microbial film, sludge, including the acid mix, may be removed from the mixture in the trickling filter.

In one or more embodiments of the invention, the sludge are received in a multi-bag filter system having a number of bags, where each bag includes a pleated cartridge housed in a vessel and is configured to remove oils and particles from the acid mix. The sludge may be received by the multi-bag filter system after being received by the trickling filter. Alternatively, the mixture may be received by the multi-bag filter system in order to separate the acid mix from the mixture.

In one or more embodiments of the invention, the acid mix may also be received in a heat exchanger, which heats the acid mix to a temperature above the boiling point of each of the acids in the acid mix (e.g., 170° F. for carbonic acid), but below the boiling point of water (i.e., 212° F.). When heated above its boiling point, each of the acids in the acid mix may be converted from a liquid state to a gaseous state. The acid mix received by the heat exchanger may first be received by the trickling filter and/or the multi-bag filter system. In one or more embodiments of the invention, the acid mix, which may include wastewater, one or more acids in liquid form, and one or more acids in gaseous form, is sent from the heat exchanger to a steam separator. The steam separator may remove the one or more acids in gaseous form from the wastewater and one or more acids in liquid form.

In one or more embodiments of the invention, the one or more acids in gaseous form removed from the mixture by the steam separator may be sent to a distiller, which purifies the one or more acids in gaseous form by removing any remaining wastewater not removed by the steam separator from the one or more acids in gaseous form. The distiller may send the one or more acids in gaseous form to a condenser, which cools the one or more acids in gaseous form to a temperature below the boiling point of each of the one or more acids in gaseous form. Cooling the one or more acids in gaseous form may convert each of the one or more acids in gaseous form to liquid form. In one or more embodiments of the invention, the distiller also separates each of each of the one or more acids in gaseous form from each other. The distiller may also send each of the one or more acids in gaseous form individually to its own condenser, rather than sending a combination of all acids in gaseous form to a single condenser.

In one or more embodiments of the invention, the mixture and/or acid mix is received by the trickling filter, multi-bag filter system, condenser, steam separator, distiller, and/or heat exchanger in any order. Further, the mixture and/or acid mix may be received by any or all of the trickling filter, multi-bag filter system, condenser, steam separator, distiller, and heat exchanger multiple times.

In Step 206, the liquid carbonic acid is pressurized to generate pressurized liquid carbonic acid. In one or more embodiments, the liquid carbonic acid is pressurized to 150 psi. The liquid carbonic acid may be pressurized using a pump. Other acids, such as sulfuric acid and nitric acid, may also be pressurized.

In Step 208, the pressurized liquid carbonic acid is combined with a liquid reagent in a hydrolysis chamber. In one or more embodiments of the invention, the liquid reagent used in combination with the pressurized liquid carbonic acid is lithium aluminum hydride ($LiAlH_4$). The lithium aluminum hydride may also be pressurized when combined with the carbonic acid. Other liquid reagents may be used in combination with the pressurized liquid carbonic acid and/or with other pressurized liquid acids (e.g., nitric acid, sulfuric acid). The acid and the reagent combined in the hydrolysis chamber may each first be sent through a control valve, which modulates the pressure and flow of the acid and/or reagent to maintain an even distribution of the acid and/or reagent in the hydrolysis chamber.

Multiple other liquid reagents may be used in combination with a pressurized liquid acid. For example, ethanol is a versatile solvent, miscible with water and many organic solvents such as acetic acid, acetone, benzene, carbon tetrachloride, chloroform, diethyl ether, ethylene glycol, glycerol, nitromethane, pyridine, and toluene. Ethanol is also miscible with light aliphatic hydrocarbons, such as pentane and hexane, and with aliphatic chlorides such as trichloroethane and tetrachloroethylene. Ethanol's miscibility with water contrasts with that of longer-chain alcohols (i.e., five or more carbon atoms), whose water miscibility decreases sharply as the number of carbons increases. The miscibility of ethanol with alkanes is limited to alkanes up to undecane. Mixtures with dodecane and higher alkanes show a miscibility gap below a certain temperature (about 13° C. for dodecane). The miscibility gap tends to get wider with higher alkanes, and the temperature for complete miscibility increases.

In Step 210, an alcohol is created from combining the pressurized liquid carbonic acid and the liquid reagent. In one or more embodiments of the invention, the alcohol is a primary alcohol. The alcohol may also be a secondary alcohol or a tertiary alcohol. The type of alcohol created may depend on the pressurized liquid acid and liquid reagent used. A primary alcohol is created when pressurized liquid carbonic acid is combined with liquid lithium aluminum hydride. Specifically, the reaction creates the following primary alcohol:

$$HOCH_2-(CH_2)_8-CH_2OH.$$

As another example, when the pressurized liquid acid is sulfuric acid and the liquid reagent is an alkene, secondary (e.g., RR'CHOH) and tertiary (e.g., RR'R"COH) alcohols may be produced. As a further example, when the pressurized liquid acid is nitric acid and the liquid reagent is R—O—H (alcohol), the reaction creates the following nitrate esters:

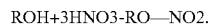

$$ROH + 3HNO3 \rightarrow RO-NO2.$$

Alcohol may be any organic compound in which a hydroxyl functional group (—OH) is bound to a carbon atom connected to another carbon or hydrogen atoms. Among the simple alcohols are acyclic alcohols, the general formula for which is $C_nH_{2n+1}OH$. Common among acyclic alcohols is ethanol ($C_2H_5OH$), which is a commonly used alcohol and is the type of alcohol found in alcoholic beverages. Other alcohols are usually described with a clarifying adjective, as in isopropyl alcohol (propan-2-ol) or wood alcohol (methyl alcohol, or methanol). The suffix -ol is designated as the chemical name of all alcohols by the International Union of Pure and Applied Chemistry (IUPAC).

Ethanol is a clear flammable liquid that boils at 78.4° C. Ethanol may be used as an industrial solvent, a car fuel, and a raw material in the chemical industry. In the U.S. and other countries, because of legal and tax restrictions on alcohol consumption, ethanol destined for other uses often contains additives that make it unpalatable (such as Bitrex) or poisonous (such as methanol). Ethanol in this form is known generally as denatured alcohol; when methanol is used, it may be referred to as methylated spirits ("Meths") or "surgical spirits".

The simplest alcohol is methanol, $CH_3OH$, which was formerly obtained by the distillation of wood and therefore is called "wood alcohol". Methanol is a clear liquid resembling ethanol in smell and properties, with a slightly lower boiling point (64.7° C.). Methanol is used mainly as a solvent, fuel, and raw material. Unlike ethanol, methanol is extremely toxic. One sip (as little as 10 ml) of methanol by a human may cause permanent blindness by destruction of the optic nerve, and 30 ml (one fluid ounce) may potentially be fatal.

Two other common alcohols are propanol and butanol. Like ethanol, propanol and butanol may be produced using a fermentation processes. In the case of propanol and butanol, though, the fermenting agent is a bacterium (*Clostridium acetobutylicum*), which feeds on cellulose. For ethanol, the fermenting agent (i.e., yeast) feeds on sugars like the *Saccharomyces*.

In the IUPAC system, the name of the alkane chain loses the terminal "e" and adds "ol" (e.g., "methanol" and "ethanol"). When necessary, the position of the hydroxyl group may be indicated by a number between the alkane name and the "ol." For example, propan-1-ol is a name used for $CH_3CH_2CH_2OH$, and propan-2-ol is a name used for $CH_3CH(OH)CH_3$. Sometimes, the position number may be written before the IUPAC name, such as 1-propanol and 2-propanol. If a higher priority group is present (such as an aldehyde, ketone or carboxylic acid), then it may be necessary to use the prefix "hydroxy", such as 1-hydroxy-2-propanone for $CH_3COCH_2OH$.

The IUPAC nomenclature may be used in scientific publications and where precise identification of the substance may be important. In other less formal contexts, an alcohol is often called by the name of the corresponding alkyl group followed by the word "alcohol" (e.g., methyl alcohol, ethyl alcohol). Propyl alcohol may be called n-propyl alcohol or isopropyl alcohol, depending on whether the hydroxyl group is bonded to the 1st or 2nd carbon on the propane chain.

Alcohols are classified as primary, secondary and tertiary alcohols, based on the number of carbon atoms connected to the carbon atom that bears the hydroxyl group. Each classification of alcohol may have a general formula. For example, the general formula for primary alcohols is $RCH_2OH$; the general formula for secondary alcohols is $RR'CHOH$; and the general formula for tertiary alcohols is $RR'R''COH$, where R, R' and R'' stand for different alkyl groups. Ethanol and n-propyl alcohol are primary alcohols. Isopropyl alcohol is a secondary alcohol. The prefixes sec- (or s-) and tert- (or t-), are conventionally shown in italics and may be used before the alkyl group's name to distinguish secondary and tertiary alcohols, respectively, from primary alcohol. For example, isopropyl alcohol is occasionally called sec-propyl alcohol, and the tertiary alcohol $(CH_3)_3COH$ (or 2-methylpropan-2-ol in IUPAC nomenclature) is commonly known as tert-butyl alcohol or tert-butanol. The following is a table of common alcohols.

| Chemical Formula | IUPAC Name | Common Name |
|---|---|---|
| Common Alcohols | | |
| Monohydric alcohols | | |
| $CH_3OH$ | Methanol | Wood alcohol |
| $C_2H_5OH$ | Ethanol | Grain alcohol |
| $C_5H_{11}OH$ | Pentanol | Amyl alcohol |
| $C_{16}H_{33}OH$ | Hexadecan-1-ol | Cetyl alcohol |
| Polyhydric alcohols | | |
| $C_2H_4(OH)_2$ | Ethane-1,2-diol | Ethylene glycol |
| $C_3H_5(OH)_3$ | Propane-1,2,3-triol | Glycerin |
| $C_4H_6(OH)_4$ | Butane-1,2,3,4-tetraol | Erythritol |
| $C_5H_7(OH)_5$ | Pentane-1,2,3,4,5-pentol | Xylitol |
| $C_6H_8(OH)_6$ | Hexane-1,2,3,4,5,6-hexol | Mannitol, Sorbitol |
| $C_7H_9(OH)_7$ | Heptane-1,2,3,4,5,6,7-heptol | Volemitol |
| Unsaturated aliphatic alcohols | | |
| $C_3H_5OH$ | Prop-2-ene-1-ol | Allyl alcohol |
| $C_{10}H_{17}OH$ | 3,7-Dimethylocta-2,6-dien-1-ol | Geraniol |
| $C_3H_3OH$ | Prop-2-in-1-ol | Propargyl alcohol |
| Alicyclic alcohols | | |
| $C_6H_6(OH)_6$ | Cyclohexane-1,2,3,4,5,6-geksol | Inositol |
| $C_{10}H_{19}OH$ | 2-(2-propyl)-5-methyl-cyclohexane-1-ol | Menthol |

The hydroxyl group generally makes the alcohol molecule polar. Those groups can form hydrogen bonds to one another and to other compounds. This hydrogen bonding means that alcohols can be used as protic solvents. Two opposing solubility trends in alcohols are: the tendency of the polar OH to promote solubility in water, and the tendency of the carbon chain to resist it. Thus, methanol, ethanol, and propanol are miscible in water because the hydroxyl group wins out over the short carbon chain. Butanol, with a four-carbon chain, is moderately soluble because of a balance between the two trends. Alcohols of five or more carbons are effectively insoluble in water because of the hydrocarbon chain's dominance. All simple alcohols are miscible in organic solvents.

Because of hydrogen bonding, alcohols tend to have higher boiling points than comparable hydrocarbons and ethers. The boiling point of the alcohol ethanol is 78.29° C., compared to 69° C. for the hydrocarbon hexane, and 34.6° C. for diethyl ether. Alcohols, like water, can show either acidic or basic properties at the O—H group. With a $pK_a$ of around 16-19, alcohols are generally slightly weaker acids than water, but alcohols are still able to react with strong bases (e.g., sodium hydride) or reactive metals (e.g., sodium). The salts that result when using alcohol in a reaction are called alkoxides, with the general formula $RO^-M^+$. Meanwhile the oxygen atom has lone pairs of non-bonded electrons that render it weakly basic in the presence of strong acids such as sulfuric acid.

Alcohols may undergo oxidation to transform into aldehydes, ketones, or carboxylic acids. Alcohols may also be dehydrated to transform into alkenes. Alcohols may further react to form ester compounds. Alcohols may still further undergo nucleophilic substitution reactions. The lone pairs of electrons on the oxygen of the hydroxyl group also make alcohols nucleophiles.

Comparing primary, secondary, and tertiary alcohols with the same chemical backbone, the hydrogen bond strength, the boiling point, and the acidity typically decrease moving from the primary alcohol to the tertiary alcohol. Some alcohols, mainly ethanol and methanol, may be used as an alcohol fuel. Fuel performance may be increased in forced-induction internal-combustion engines by injecting alcohol into the air intake after the turbocharger or supercharger has pressurized the air. Injecting alcohol cools the pressurized air, providing a denser air charge, which allows for more fuel, and therefore more power.

Alcohols have applications in industry and science as reagents or solvents. Because of its low toxicity and ability to dissolve non-polar substances, ethanol can be used as a solvent in medical drugs, perfumes, and vegetable essences such as vanilla. In organic synthesis, alcohols serve as versatile intermediates. Ethanol may also be used as an antiseptic to disinfect the skin before injections are given, often along with iodine. Ethanol-based soaps are becoming common in restaurants and are convenient because they do not require drying due to the volatility of the compound. Alcohol is also used as a preservative for laboratory specimens.

Primary alkyl halides react with aqueous NaOH or KOH mainly to give primary alcohols in nucleophilic aliphatic substitution. (Secondary and especially tertiary alkyl halides will give the elimination (alkene) product instead). Grignard reagents react with carbonyl groups to secondary and tertiary alcohols. Related reactions are the Barbier reaction and the Nozaki-Hiyama reaction. Aldehydes or ketones are reduced with sodium borohydride or lithium aluminium hydride. Another reduction by aluminium isopropylates is the Meerwein-Ponndorf-Verley reduction. Noyori asymmetric hydrogenation is the asymmetric reduction of β-keto-esters.

Alkenes engage in an acid-catalysed hydration reaction using concentrated sulfuric acid as a catalyst, which usually gives secondary or tertiary alcohols. The hydroboration-oxidation and oxymercuration-reduction of alkenes are more reliable in organic synthesis. Alkenes react with NBS and water in a halohydrin formation reaction. Amines may be converted to diazonium salts, which are then hydrolyzed.

Alcohols can behave as weak acids, undergoing deprotonation. The deprotonation reaction to produce an alkoxide salt is either performed with a strong base such as sodium hydride or n-butyllithium, or with sodium or potassium metal.

$$2R-OH + 2NaH \rightarrow 2R-O^-Na^+ 2H_2\uparrow$$

$$2R-OH + 2Na \rightarrow 2R-O^-Na + H_2$$

E.g. $2CH_3CH_2-OH + 2Na \rightarrow 2CH_3-CH_2-O^-Na + H_2$

Water is similar in $pK_a$ to many alcohols, so with sodium hydroxide there is an equilibrium set up which usually lies to the left:

$$R-OH + NaOH \mathrel{<=>} R-O^-Na^+ + H_2O \text{(equilibrium to the left)}$$

It should be noted, though, that the bases used to deprotonate alcohols are strong themselves. The bases used and the alkoxides created are both highly moisture sensitive chemical reagents.

The acidity of alcohols may also be affected by the overall stability of the alkoxide ion. Electron-withdrawing groups attached to the carbon containing the hydroxyl group may serve to stabilize the alkoxide when formed, thus resulting in greater acidity. On the other hand, the presence of electron-donating group may result in a less stable alkoxide ion that is formed. As a result, the unstable alkoxide ion that is formed may tend to accept a proton to reform the original alcohol.

With alkyl halides, alkoxides give rise to ethers in the Williamson ether synthesis. The OH group may not be a good leaving group in nucleophilic substitution reactions, so neutral alcohols tend not to react in such reactions. However, if the oxygen is first protonated to give $R-OH_2^+$, the leaving group (water) is much more stable, and the nucleophilic substitution may take place. For instance, tertiary alcohols react with hydrochloric acid to produce tertiary alkyl halides, where the hydroxyl group is replaced by a chlorine atom by unimolecular nucleophilic substitution. If primary or secondary alcohols are to be reacted with hydrochloric acid, an activator such as zinc chloride is needed.

Alcohols may likewise be converted to alkyl bromides using hydrobromic acid or phosphorus tribromide. As an example:

$$3R-OH + PBr_3 \rightarrow 3RBr + H_3PO_3$$

In the Barton-McCombie deoxygenation, an alcohol is deoxygenated to an alkane with tributyltin hydride or a trimethylborane-water complex in a radical substitution reaction. Alcohols are themselves nucleophilic, so $R-OH_2^+$ can react with ROH to produce ethers and water in a dehydration reaction, although this reaction is rarely used outside of the manufacture of diethyl ether. More useful is the E1 elimination reaction of alcohols to produce alkenes. The E1 elimination reaction of alcohols generally obeys Zaitsev's Rule, which states that the most stable (usually the most substituted) alkene is formed. Tertiary alcohols eliminate easily at just above room temperature, but primary alcohols require a higher temperature. A more controlled elimination reaction is the Chugaev elimination with carbon disulfide and iodomethane.

To form an ester from an alcohol and a carboxylic acid, the reaction, known as Fischer esterification, is usually performed at reflux with a catalyst of concentrated sulfuric acid:

$$R-OH + R'-COOH \rightarrow R'-COOR + H_2O$$

In order to drive the equilibrium to the right and produce a good yield of ester, water is usually removed, either by an excess of $H_2SO_4$ or by using a Dean-Stark apparatus. Esters may also be prepared by reaction of the alcohol with an acid chloride in the presence of a base such as pyridine. Other types of ester may be prepared similarly. For example, tosyl (tosylate) esters are made by reaction of the alcohol with p-toluenesulfonyl chloride in pyridine.

Primary alcohols ($R-CH_2-OH$) may be oxidized either to aldehydes ($R-CHO$) or to carboxylic acids ($R-CO_2H$), while the oxidation of secondary alcohols ($R^1R^2CH-OH$) normally terminates at the ketone ($R^1R^2C=O$) stage. Tertiary alcohols ($R^1R^2R^3C-OH$) are resistant to oxidation. The direct oxidation of primary alcohols to carboxylic acids normally proceeds via the corresponding aldehyde, which is transformed via an aldehyde hydrate ($R-CH(OH)_2$) by reaction with water before it can be further oxidized to the carboxylic acid.

Reagents useful for the transformation of primary alcohols to aldehydes may normally also be suitable for the oxidation of secondary alcohols to ketones. Such reagents include Collins reagent and Dess-Martin periodinane. The direct oxidation of primary alcohols to carboxylic acids can be carried out using Potassium permanganate or the Jones reagent.

The following describes an example in accordance with one or more embodiments of the invention. The example is for explanatory purposes only and is not intended to limit the scope of the invention. Terminology used in FIGS. 1 and 2 may be used in the example without further reference to FIGS. 1 and 2.

Example 1

Combustion Process

Figure 3:
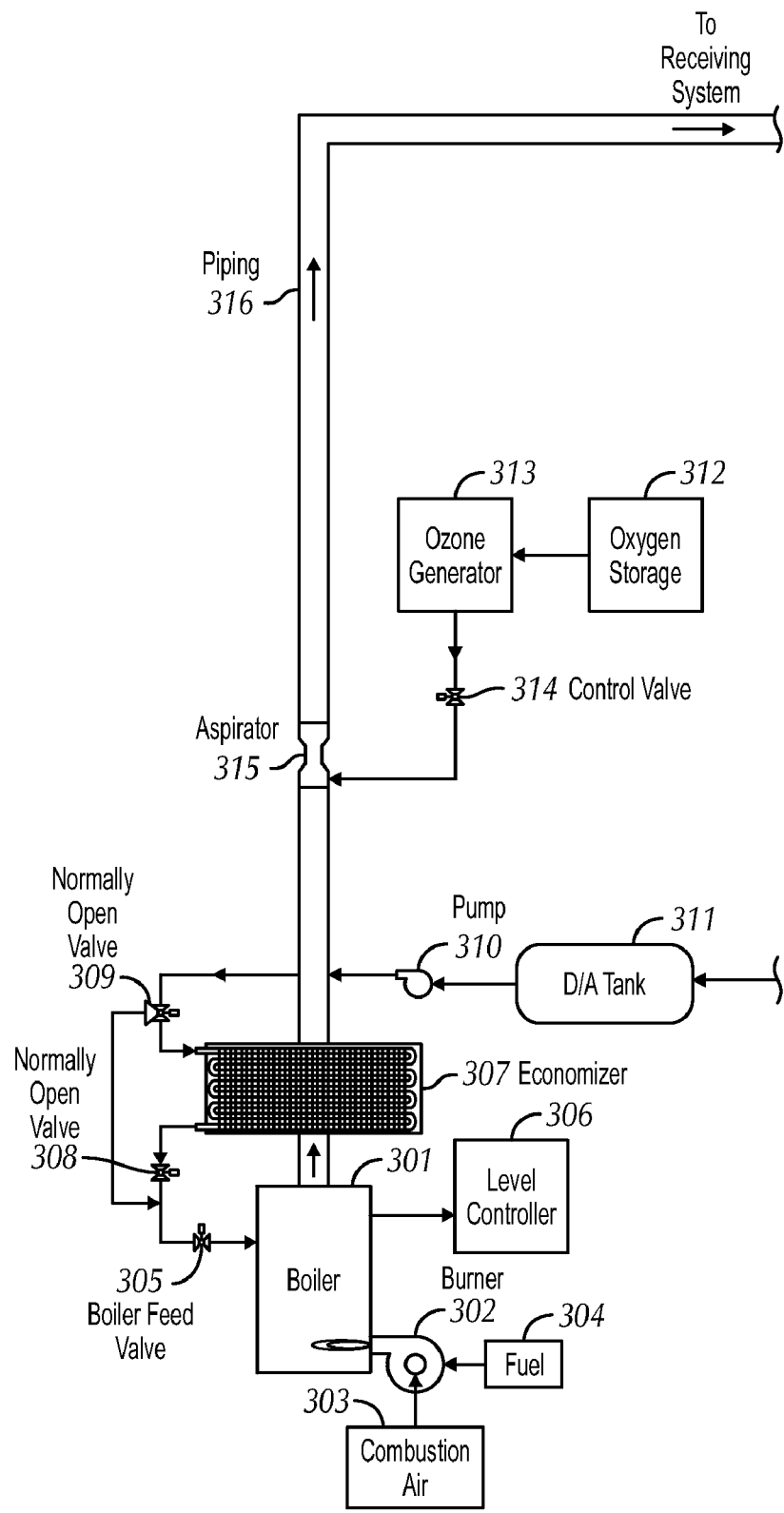
FIG. 3 shows a single line diagram of an example system for creating a stream of flue gas containing $CO_2$ from a combustion process in accordance with one or more embodiments of the invention.

Consider the following example, shown in FIG. 3, which describes a combustion process that produces a stream of flue gas, which is used in accordance with one or more embodiments described above. Specifically, FIG. 3 illustrates a heat recovery and pollution abatement apparatus that is designed for numerous applications utilized with fossil fueled boilers such as those applied within coal-fired generating facilities and industrial process plants. In one or more embodiments, the boiler (301) is a fire-tube or water-tube boiler capable of producing millions of BTUs per hour of steam used to produce electricity. The boiler (301) may utilize a conventional design that includes a burner (302) which receives a controlled quantity of combustion air (303) and fuel (304) (e.g., coal, natural gas).

The boiler exhaust gas may flow through a high temperature economizer (307), which removes heat from the exhaust gases after exiting the boiler. The economizer (307) may be a forced-flow, once through conversion heat transfer device, usually consisting of steel tubes, to which feed-water is supplied at a pressure above that of the steam generating section and at a rate corresponding to the steam output of the boiler unit. An economizer (307) may be classed in a number of different ways. For example, an economizer may be classified as horizontal or vertical-tube type, according to its geometrical arrangement. An economizer (307) may also be classified as longitudinal or cross flow, depending upon the direction of gas-flow with respect to the tubes of the economizer (307). An economizer may further be characterized as parallel or counter flow, with respect to the relative direction of gas and water flow. An economizer (307) may still further be characterized as steaming or non-steaming, depending on the thermal performance. Other examples of economizer classification include return-bend or continuous-tube (depending upon the details of design) and base-tube or extended-surface (according to the type of heat-absorbing surface). Staggered or in-line tube arrangements may be used in an economizer The arrangement of tubes in an economizer (307) affects a number of factors, including but not limited to the gas flow through the tube bank, the draft loss, the heat transfer characteristics, and the ease of cleaning.

Water in a boiler lost to steam (commonly called "boiler make-up" or "boiler feed water") may be supplied by a pump (310) from a source of water through a condensing economizer to a deaeration (D/A) tank (311). From the deaeration tank (311) the boiler feed water may be fed by a boiler feed pump (310) through a normally open valve (309) to the economizer (307). In one or more embodiments, the boiler feed water is increased in temperature from about 220° F. to about 280° F. by the economizer (307). The boiler feed water, at the elevated temperature, may be fed from the economizer (307) through a normally open valve (308) to a boiler feed valve (305). The boiler feed valve (305) may be regulated by a level controller (306) to maintain a preselected volume of boiler feed water in the boiler (301).

In one or more embodiments, the exhaust gas (i.e., flue gas) exiting the economizer (307) is at a temperature of about 320° F. and is directed through an aspirator (315). In one or more embodiments, oxygen from an oxygen storage tank (312) is supplied to an ozone generator (313) where $O_3$ (ozone) is generated and subsequently directed through a control valve (314) to modulate the ozone gas to the specific requirements needed to mix with the flue gas from the economizer. From the control valve (314) the ozone gas may enter the aspirator (315) to act as a reagent.

In one or more embodiments, the aspirator (315) is a flow-through nozzle device in which the kinetic energy of a substance is increased in an adiabatic process. This increase in kinetic energy involves a decrease in pressure and is accomplished by the change in the flow area. The aspirator (315) may be a mechanical device that introduces ozone into the flow of flue gas through a nozzle where the ozone is mixed with the flue gas flow using the ozone as an oxidizing agent to convert nitric oxide (NO) to nitrogen dioxide (NO2). In one or more embodiments, the ozone is introduced to the flue gas at 1.1 stoichiometric concentration. The introduction of ozone gas into the flue gas stream causes the following reaction to occur:

$$NO+O_3 \rightarrow NO_2+O_2$$

This reaction is required as $NO_2$, and not NO, is needed to convert $NO_X$ into nitric acid for removal from the flue gas stream. The flue gas may then be sent through piping (316) to a receiving system (e.g., the COMPLY 2000 Unit, as described below in Example 2).

Example 2

Receiving System

Figure 4:
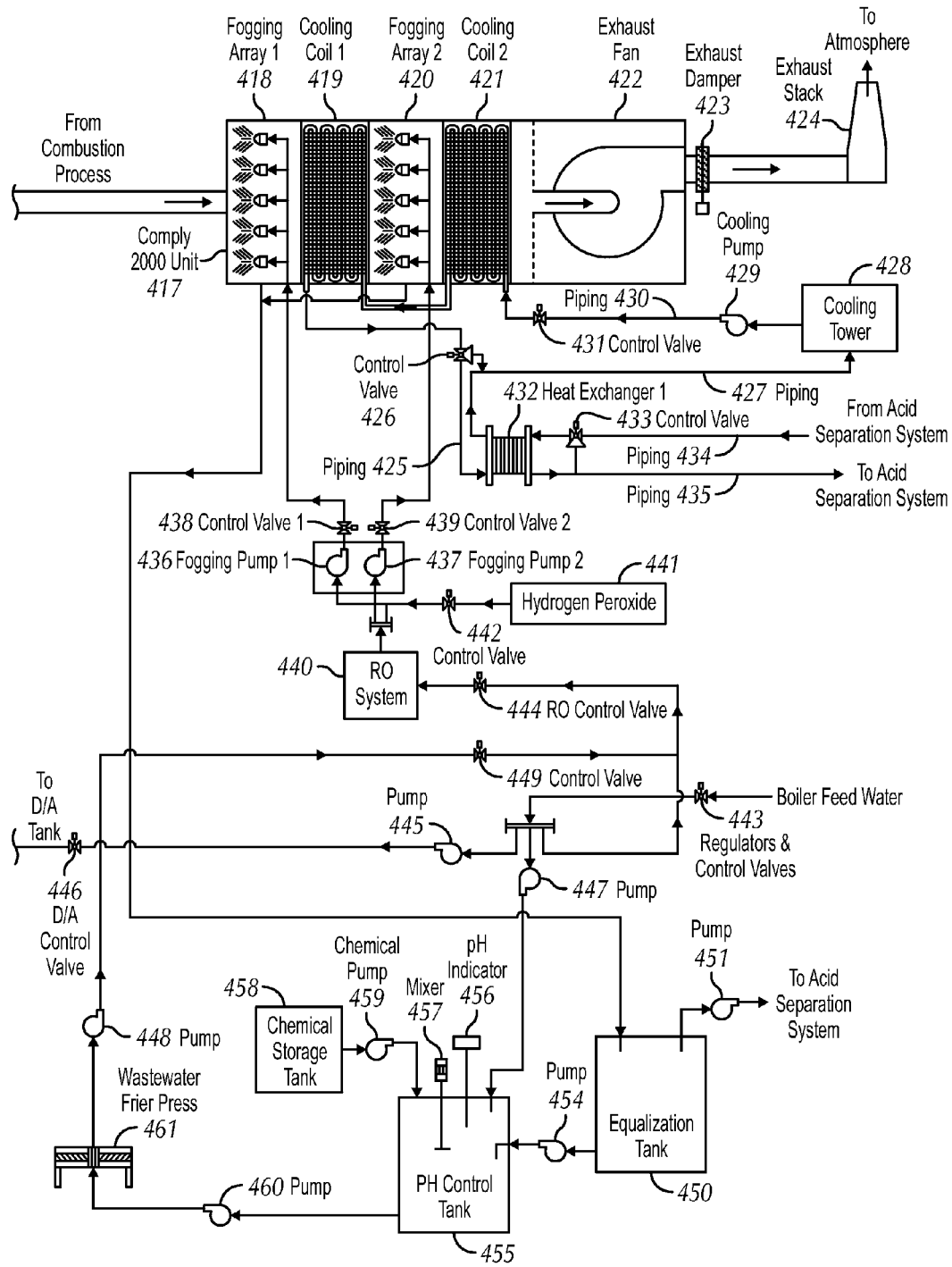
FIG. 4 shows a single line diagram of an example system for receiving a stream of flue gas from the combustion process and converting $CO_2$ from the flue gas to an acid in accordance with one or more embodiments of the invention.

Consider an example, shown in FIG. 4, which describes a receiving system to receive a stream of flue gas in accordance with one or more embodiments described above. Specifically, the receiving system in FIG. 4 represents the COMPLY 2000, introduced above. Those of skill in the art will appreciate that other systems may exist to receive a stream of flue gas and generate a mixture of carbonic acid (as well as, in some cases, sulfuric acid, nitric acid, and/or other acids) and wastewater.

In one or more embodiments, a stream of flue gas, as from the aspirator as described above with respect to FIG. 3, is directed to the COMPLY 2000 Unit (417) through a series of metal breeching. The COMPLY 2000 Unit (417) includes a first stage having fogging array 1 (418) and cooling coil 1 (419), as well as a second stage also having fogging array 2 (420) and cooling coil 2 (421). The flue gas enters the first stage of the COMPLY 2000 Unit (417) and comes into contact with fogging array 1 (418). Fogging array 1 (418) sprays a liquid solution directed against the flue gas flow, creating a hydrolysis reaction. Each fogger in fogging array 1 (418) may be configured to release a high pressure liquid solution in droplets that are very small (about 10 microns in diameter) and cover a large surface area, which enables the COMPLY 2000 Unit (417) to react with the CO2 from the flue gas to create liquid carbonic acid, which is removed with the wastewater from the process.

In one or more embodiments, the liquid solution starts from RO (reverse osmosis) water, created by the RO system (440), that is mixed with hydrogen peroxide (441) at 2% concentration before entering fogging pump 1 (436). Fogging pump 1 (436) may increase the pressure of the mixture of the RO water and hydrogen peroxide (441). The hydrogen peroxide (441) may be modulated and controlled by a control valve (442) to ensure proper mixing with the RO water. The RO system (440) may be a filtration system configured to remove large molecules and ions from the liquid solution by applying pressure to the liquid solution when it is on one side of a selective membrane within the RO system (440). As a result, the solute (i.e., large molecules or ions) may be retained on the pressurized side of the selective membrane, and the pure solvent (i.e., liquid solution) may be allowed to pass through the holes in the selective membrane to the other, less pressurized side of the selective membrane.

In industry, the RO system (440) may be used to remove minerals from boiler feed water at power plants. Because the boiler feed water is boiled and condensed repeatedly, the boiler feed water needs to be as pure as possible so that the boiler feed water does not leave mineral or other deposits on the machinery or cause corrosion. Such deposits inside or outside the boiler tubes may result in under-performance of the boiler system, which may reduce the efficiency of the boiler system and result in poor steam production, which in turn may lead to poor power production at the turbine and/or degradation of the turbines blades.

In one or more embodiments, fogging pump 1 (436) draw the mixture of the RO water and hydrogen peroxide (441) and direct the mixture to control valve 1 (438). Control valve 1 (438) modulates the mixture and distributes an even flow of the mixture to fogging array 1 (418) in the first stage of the COMPLY 2000 Unit (417). The liquid solution sprayed by fogging array 1 (418) may be sprayed under pressure. An example pressure at which the liquid solution may be spayed by fogging array 1 (418) is approximately 1000 psi. In one or more embodiments, the liquid solution is sprayed against the flow of the stream of flue gas. In one or more embodiments, when the droplets of liquid solution come in contact with the contaminants (e.g., carbonic acid) in the flue gas, the droplets of liquid solution (i.e., the mixture) absorb the contaminants. For example, the introduction of the liquid solution of $H_2O$ (water) and $H_2O_2$ (Hydrogen Peroxide (441)) to the flue gas may cause the following reactions to occur:

$$3NO_2+H_2O \rightarrow 2HNO_3+NO$$

$$SO_2+H_2O_2 \& H_2SO_4$$

$$CO_2+H_2O \rightarrow H_2CO_3 \rightarrow HCO_3+H^+$$

In one or more embodiments, after passing through fogging array 1 (418) in the first stage of the COMPLY 2000 Unit (417), the flue gas then passes over cooling coil 1 (419), also located in the first stage of the COMPLY 2000 Unit (417).

When the flue gas passes over cooling coil 1 (419), an amount of heat is removed from the flue gas. When the flue gas is cooled, a water film may develop on cooling coil 1 (419). In one or more embodiments, this water film is used to capture the $HNO_3$, H2SO4, and $H_2CO_3$, each now in liquid form. A mixture of the water film (i.e., wastewater) and the liquid acids (e.g., $HNO_3$, H2SO4, and $H_2CO_3$) may be removed from cooling coil 1 (419) to an equalization tank (450). The equalization tank (450) may be part of the COMPLY 2000 Unit (417), or the equalization tank (450) may be part of a separate wastewater containment facility.

In one or more embodiments, after passing through cooling coil 1 (419) in the first stage of the COMPLY 2000 Unit (417), the flue gas passes through a second stage of the COMPLY 2000 Unit (417), which is configured substantially similar to the first stage of the COMPLY 2000 Unit (417). In other words, the second stage of the COMPLY 2000 Unit (417) may include fogging array 2 (420) and cooling coil 2 (421). The second stage of the COMPLY 2000 Unit (417) (as well as each additional stage, if any) may be used to capture flue gas contaminants are not captured in the first stage. The process described above with respect to the first stage, including fogging array 1 (418) and cooling coil 1 (419) is repeated in the second stage with fogging array 2 (420) and cooling coil 2 (421).

In one or more embodiments, a mixture of RO water and hydrogen peroxide (441) may be sprayed into the flue gas in the second stage of the COMPLY 2000 Unit (417). The mixture may be the same mixture used in the first stage, described above. The mixture may also be pressurized using fogging pump 2 (437). The flow of the mixture may be regulated by control valve 2 (439). In one or more embodiments, the wastewater and liquid acids are directed to the same equalization tank (450) described above with respect to the first stage. Alternatively, a different equalization tank (not shown) may be used to collect the wastewater and liquid acids created in the second stage.

In one or more embodiments, the flue gas, after passing through the final stage of the COMPLY 2000 Unit (417), is at a lower temperature and a reduced amount of $CO_2$ compared to when it entered the first stage. The flue gas may then be directed to atmosphere through an industrial exhaust fan (422) and exhaust damper (423) followed by an exhaust stack (424). In one or more embodiments, the exhaust damper (423) is open when a boiler generating the flue gas (e.g., boiler (301) as described with respect to FIG. 3 above) and the Comply 2000 Unit (417) are operational. The exhaust damper (423) may be closed during shut down of the boiler and/or associated equipment.

As described above, the cooling coil in each stage (e.g., cooling coil 1 (419) and cooling coil 2 (421)) may reduce the temperature of the flue gas as the flue gas is directed through each fogging array (e.g., fogging array 1 (418), fogging array 2 (420)). The flue gas temperature entering the first stage of the Comply 2000 unit (417) may be approximately 320° F. In the first stage, the temperature of the flue gas may decrease to approximately to 280° F. as fogging array 1 (418) increases the humidity without saturating the flue gas. After the flue gas is directed through cooling coil 1 (419) in the first stage, the flue gas temperature may decrease to approximately 160° F., where the flue gas enters the second stage. Fogging array 2 (420) in the second stage again may increase the humidity of the flue gas to near-saturation, further decreasing temperature of the flue gas. When the flue gas passes through cooling coil 2 (421) in the second stage, the temperature of the flue gas temperature may become as low as 100° F.

In one or more embodiments, each cooling coil (e.g., cooling coil 1 (419), cooling coil 2 (421)) are designed for high temperature and corrosive moisture conditions. Each cooling coil may be certified by the ARI (now known as the Air-Conditioning, Heating, and Refrigeration Institute) or similar authority. Further, each cooling coil may be verified in accordance with the ARI 410 certification program. In one or more embodiments, the cooling coils are copper tube finned where the tube fin surfaces are individually wound to each tube, enabling the cooling coil to expand and contract without stressing the fin/tube bond. Each tube of the cooling coils may be silver soldered to the header and return bends to allow high working pressure capabilities.

Intermediate tube support may be welded to the casing on each cooling coil with normal tube length over 40" to reduce sagging common with large coils. All cooling coils may be dipped in a Heresite® protective coating. (Heresite is a registered trademark of Heresite Protective Coatings, Inc. of Manitowoc, Wis.) The cooling coils are mounted in the COMPLY 2000 Unit (417) on tracks for lateral withdrawal. The headers for the cooling coils may be constructed of heavy gage steel. The casing for the cooling coils may be constructed and welded of heavy gage steel to ensure that the cooling coils may be stacked without support.

In one or more embodiments, specifically for a COMPLY 2000 Unit (417) with two stages, the water feeding the cooling coils (i.e., cooling coil (419) and cooling coil (421)) is drawn from a cooling tower (428) through a cooling pump (429). The water may first be delivered from the cooling tower (428) to cooling coil 2 (421) of the second stage through a series of piping (430) and a control valve (431). The temperature of the water delivered to cooling coil 2 (421) of the second stage may be approximately 70° F. When the water leaves cooling coil 2 (421) of the second stage for delivery to cooling coil 1 (419) of the first stage, its temperature may be heated up to approximately to 110° F. The cooling coils of the first and second stage may be connected in series to maximize the heat that is being extracted from the flue gas. After flowing through cooling coil 1 (419) of the first stage, the water temperature may in crease to approximately 220° F.

In one or more embodiments, once leaving cooling coil 1 (419) of the first stage, the water is then directed to a control valve (426) and a network of piping (425) connected to heat exchanger 1 (432). In one or more embodiments of the invention, the other fluid used in heat exchanger 1 (432) is one or more liquid acids from the acid separation system, described below with respect to Example 3. The other fluid used in heat exchanger 1 (432) may be delivered to heat exchanger 1 (432) by a network of piping (434) and a control valve (433), which regulates the flow of the other fluid into heat exchanger 1 (432). In one or more embodiments, after being heated, the other fluid leaves heat exchanger 1 (432) through a network of piping (435).

In one or more embodiments, after the water flows through heat exchanger 1 (432), where the temperature of the water is reduced, the water is directed to the cooling tower (428) through a series of piping (427). In the cooling tower (428), the water may be further cooled before being sent back to cooling coil 2 (421) in the second stage to repeat the process.

Returning to the equalization tank (450) described above, the equalization tank (450) holds all the liquid contaminant (i.e., acids and particulates) that were removed from the flue gas in the first and second stage of the COMPLY 2000 Unit (417). The liquid acids are drawn from the equalization tank (450) and directed through a pump (451) to an acid separation system, as described, for instance, in Example 3 below. In one or more embodiments, at the bottom of the equalization tank (450), a sludge, created by removal of the particulate from the flue gas, settles and collects. A pump (454) may be used to direct the sludge to a pH control tank (455), where the sludge is diluted and neutralized.

In one or more embodiments, boiler feed water may be distributed by a series of regulators and control valves (443) through a pump (445) to a D/A tank through a D/A control valve (446). The D/A tank may be, for example, deaeration tank (311) as described above with respect to Example 1 and FIG. 3.

In one or more embodiments, boiler feed water may be distributed by a series of regulators and control valves (443) through a pump (447) to the pH control tank (455). A chemical storage tank (458) may contain reagents to neutralize acids in the pH control tank (455). The reagents in the chemical storage tank may be directed through a chemical pump (459) to the pH control tank (455), where the reagents are added to the sludge and mixed by a mixer (457). The pH level of the mixture of the sludge and reagents may be monitored during the mixing process using a pH indicator (456) located in the pH control tank (455). Reagents may be added until a pH level of the mixture has been reached and a neutralized solution has been created. From the pH control tank (455) the neutralized solution may be directed through a pump (460) to a wastewater filter press (461).

In one or more embodiments, the wastewater filter press (461) is a highly efficient, compact, dewatering device for separating solids from liquid slurries in the form of a compressed cake. The wastewater filter press (461) includes a structured framework, filter chambers (formed by recess portions in a recessed plate system, or by frames in a plate and frame system), and filter cloth. In one or more embodiments, the wastewater filter press (461) is a separation device used for solid or liquid separation that works on feed pressure or squeeze pressure to reduce liquid content in process or waste slurries or to reduce solid content in a product. The wastewater filter press (461) may consist of a series of horizontally arranged vertical filter plates, each covered with a material such as paper, felt, or a synthetic woven material. A mechanical structure called a skeleton may be used to support the filter plates, and a closure mechanism may provide the required force on the sealing faces of the plates to counteract the applied force of filtration (squeezing). The water that is pressed from the wastewater filter press (461) may be directed through a pump (448) to a control valve (449), where the water is modulated and re-introduced to the RO system (440) through the RO control valve (444).

Those skilled in the art will appreciate that receiving systems, such as the COMPLY 2000 Unit (417), may also be configured to remove other pollutants, in addition to $CO_2$, $NO_X$, and $SO_2$. Such other pollutants may include, but are not limited to, mercury (Hg) and particulate matter (e.g., PM2.5, PM10).

Example 3

Acid Separation System

Figure 5:
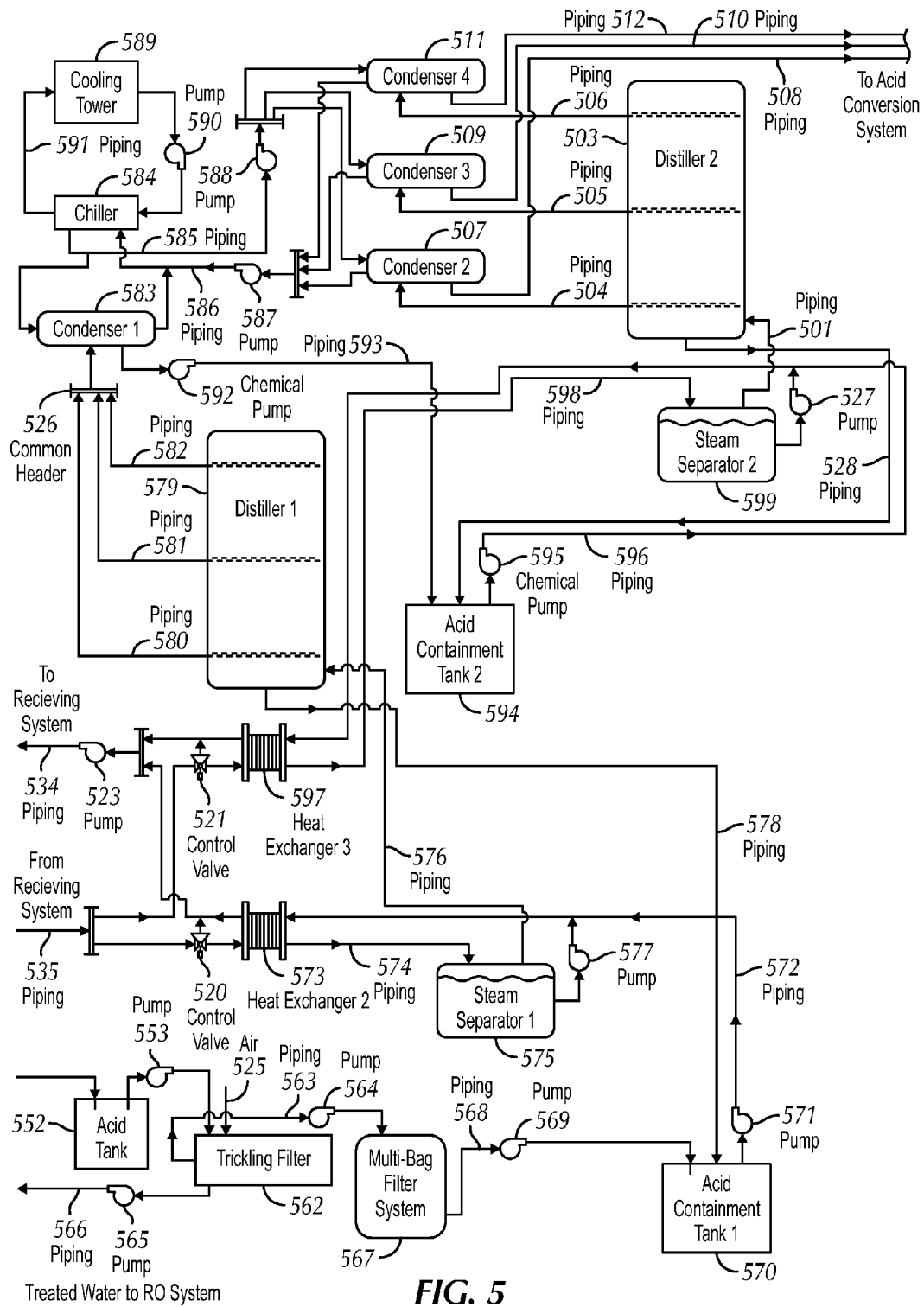
FIG. 5 shows a single line diagram of an example system for separating the acid from wastewater and purifying the acid in accordance with one or more embodiments of the invention.

Consider an example, shown in FIG. 5, which describes an acid separation system. Specifically, the acid separation system may be configured to separate acids from a mixture that includes wastewater and purify the acids. In the acid separation system, the mixture is received in liquid form from a receiving system, for example, as described above with respect to Example 2. In one or more embodiments, the mixture is received from the receiving system and stored in an acid tank (552). A pump (553) sends the mixture from the acid tank (552) to a trickling filter (562) of the acid separation system.

As described above with respect to FIG. 1, the trickling filter (562) uses air (525) to separate impurities, including acids, from the mixture to produce wastewater. The wastewater that flows out of the trickling filter (562) may be reused in a different process. In this Example 3, the wastewater from the trickling filter (562) is sent to a reverse osmosis (RO) system using a pump (565) and a series of piping (566). The RO system may be, for example, RO system (440) in the receiving system described above with respect to Example 2. The impurities separated from the mixture form sludge. As for the sludge (including the acids) created by the trickling filter (562), another series of piping (563) direct the sludge from the trickling filter (562) through a chemical pump (464) to a multi-bag filter system (567). The multi-bag filter system (567) removes oils and other particles from the sludge using bags of pleated cartridges housed in a vessel. The multi-bag filter system (567) releases liquid acids with a number of impurities. From the multi-bag filter system (567) the liquid acids are directed, using piping (568), through a chemical pump (569) to acid containment tank 1 (570).

From acid containment tank 1 (570), the liquid acids are directed through a chemical pump (571) and a series of piping (572) to heat exchanger 2 (573). In heat exchanger 2 (73), the liquid acids are heated to a temperature above the liquid acids' boiling points (e.g., between 170° F. and 185° F.), but below the boiling point of water (i.e., 212° F.). In one or more embodiments of the invention, the liquid acids are the "other fluid," as described above with respect to the heat exchanger in the receiving system of Example 2. The fluid used in heat exchanger 2 (573) to raise the temperature of the liquid acids is sent through a series of piping (535), controlling the flow and volumes of the fluid using control valves (520), before entering heat exchanger 2 (573). Upon exiting heat exchanger 2 (573), a pump (523) is used send the fluid used to heat the liquid acids through another series of pipes (534) back to the receiving system.

From heat exchanger 2 (573) the acids, now in both liquid and gaseous form, are directed into steam separator 1 (575) using piping (574). The acids in vapor form exit steam separator 1 (575) through piping (576) to be received by distiller 1 (579). The acids in liquid form exit steam separator 1 (575), using a pump (577), through piping (572) to be sent back to heat exchanger 2 (573). Distiller 1 (579) receives the acids in vapor form from steam separator 1 (575) and distills each of the different acids (e.g., $HNO_3$, $H2SO_4$, and $H_2CO_3$) individually. In this example 3, distiller 1 (579) is one large vessel with multiple compartments, one for each acid in vapor form. Distiller 1 (579) removes water from each of the acids in gaseous form. Distiller 1 (579) also collects liquids and sends the collected liquids back to acid containment tank 1 (570) by way of a series of piping (578). Distiller 1 (579) may utilize a method of separating the acids in vapor form based on differences in their volatilities in a boiling liquid mixture. Once each acid is distilled in distiller 1 (579), each acid is sent individually through piping (e.g., piping (580), (581), (582)) to a common header (526), where the acids re-mixed together.

From the common header (526), the acid vapor is sent to condenser 1 (583) where the acid vapor is exposed to a pressure below atmospheric pressure and cooled to liquefy the acid. Associated with condenser 1 (583) is a chiller (584), a cooling tower (589), a network of pipes (585), (586), (591), and a pump (590) to distribute the chilled water and condenser water to condenser 1 (583), the chiller (584), and the cooling tower (589). In one or more embodiments of the invention, the cooling tower (589) is the same cooling tower (428) in the receiving system described above with respect to Example 2 and FIG. 4. Distributing the chilled water and condenser water using this network is necessary to ensure that sufficient cooling is supplied to condenser 1 (583) so as to change the acid gases into liquid. From condenser 1 (583), the liquid acid is then directed through a chemical pump (592) and a series of piping (593) to acid containment tank 2 (594). In this Example 3, acid containment tank 2 (594) is a different acid containment tank than acid containment tank 1 (570).

From acid containment tank 2 (594) the mixed liquid acids are directed through a chemical pump (595) to heat exchanger 3 (597) by way of a series of piping (596). The liquid acids are directed through heat exchanger 3 (597) where the liquid acids are heated, as in heat exchanger 2 (573), to a temperature above the liquid acids' boiling points (e.g., between 170° F. and 185° F.), but below the boiling point of water (i.e., 212° F.). In one or more embodiments of the invention, the liquid acids are the "other fluid," as described above with respect to the heat exchanger in the receiving system of Example 2. The fluid used in the heat exchanger to raise the temperature of the liquid acids is sent through a series of pipes (535), controlling the flow and volumes of the fluid using control valves (520), before entering heat exchanger 3 (597). Upon exiting heat exchanger 3 (597), a pump (523) is used send the fluid used to heat the liquid acids through another series of pipes (534) back to the receiving system.

From heat exchanger 3 (597) the acids, now in both liquid and gaseous form, are directed into steam separator 2 (599) using piping (598). The acids in vapor form exit steam separator 2 (599) through piping (501) to be received by distiller 2 (503). The acids in liquid form exit steam separator 2 (599), using a pump (527), through piping (596) to be sent back to heat exchanger 3 (597). Distiller 2 (503) receives the acids in vapor form from steam separator 2 (599) and distills each of the different acids (e.g., $HNO_3$, $H2SO_4$, and $H_2CO_3$) individually. In this example 3, as was the case with distiller 1 (579), distiller 2 (503) is one large vessel with multiple compartments, one for each acid in vapor form. Distiller 2 (503) removes water from each of the acids in gaseous form. Distiller 2 (503) also collects liquids and sends the collected liquids back to acid containment tank 2 (594) by way of a series of piping (528). Distiller 2 (503) may utilize a method of separating the acids based on differences in their volatilities in a boiling liquid mixture. Once each acid is distilled in distiller 2 (503), each acid is sent individually through piping (e.g., piping (504), (505), (506)) to a separate condenser (e.g., condenser 2 (507), condenser 3, (509), condenser 4 (511)). Specifically, the first acid to separate is the carbonic acid because it boils at the lowest temperature and is directed out of distiller 2 (503) by way of piping (506) and is sent to condenser 4 (511). The second acid to separate is the nitric acid and is directed out of distiller 2 (503) by way of piping (505) and is sent to condenser 3 (509). The last acid in the separation process is the sulfuric acid and is directed out of distiller 2 (503) by way of piping (504) and is sent to condenser 2 (507).

In each of condenser 2 (507), condenser 3, (509), and condenser 4 (511), the individual acid vapor is exposed to a pressure below atmospheric pressure and cooled to liquefy the acid. As with condenser 1 (583), associated with condenser 2 (507), condenser 3 (509), and condenser 4 (511) is the chiller (584), the cooling tower (589), a network of pipes (585), (586), (591), and pumps (587), (588), (590) to distribute the chilled water and condenser water to condenser 2 (507), condenser 3 (509), condenser 4 (511), the chiller (584), and the cooling tower (589). Distributing the chilled water and condenser water using this network is necessary to ensure that sufficient cooling is supplied to condenser 2 (507), condenser 3 (509), and condenser 4 (511) so as to change each acid in gaseous form into liquid. From condenser 2 (507), condenser 3 (509), and condenser 4 (511), the liquid acid is then directed, using separate piping (508), (510), and (512), to the acid conversion system, as described below with respect to Example 4. Specifically, the carbonic acid is cooled down by condenser 4 (511) then sent by way of piping (512) to acid holding tank 3 (605) of the acid conversion system. The nitric acid is cooled down by condenser 3 (509) then sent by way of piping (510) to acid holding tank 2 (604) of the acid conversion system. The sulfuric acid is cooled down by condenser 2 (507) then sent by way of piping (508) to acid holding tank 1 (603) of the acid conversion system.

Example 4

Acid Separation System

Figure 6:
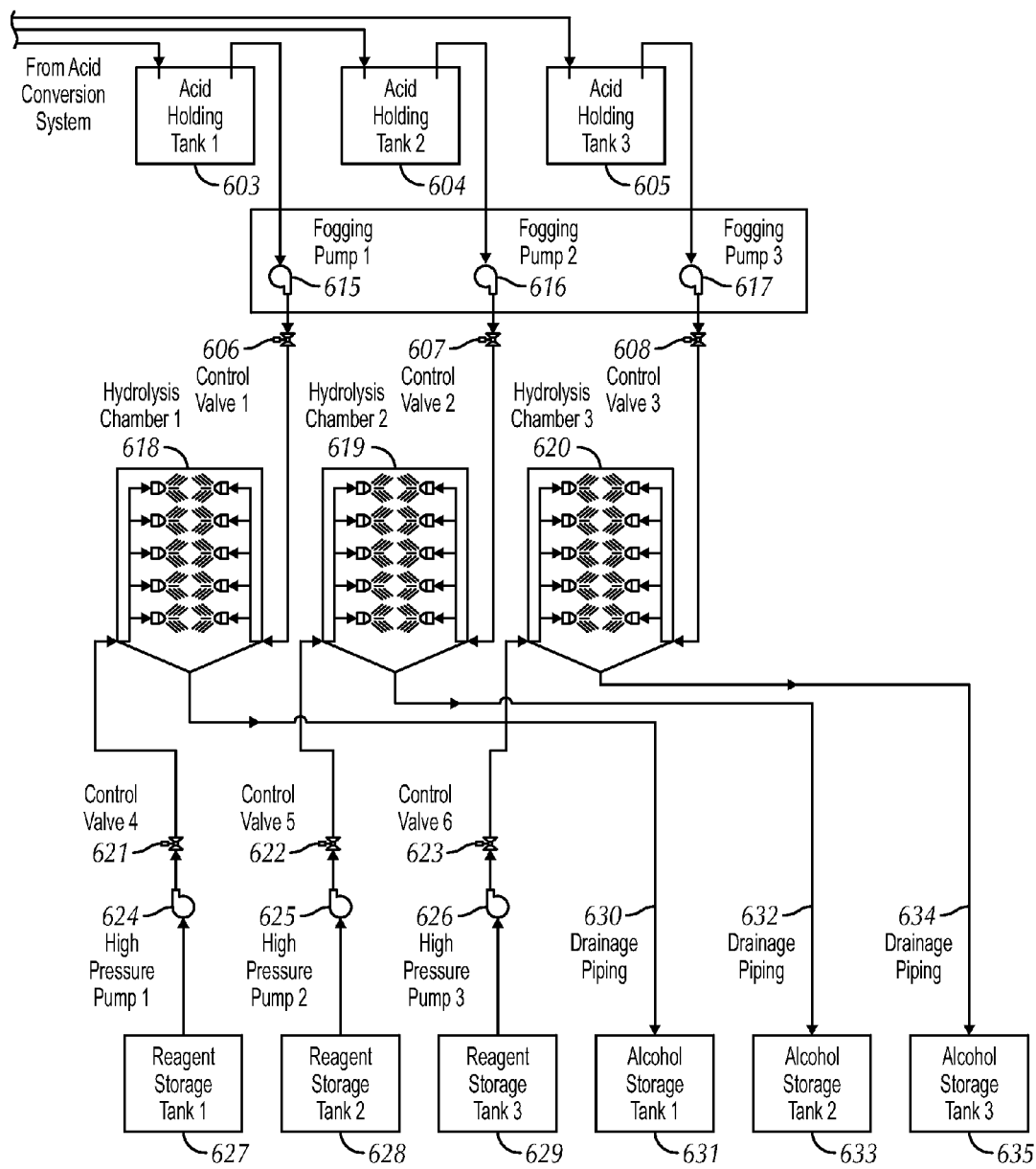
FIG. 6 shows a single line diagram of an example system for converting the purified acid to alcohol in accordance with one or more embodiments of the invention.

Consider an example, shown in FIG. 6, which describes an acid conversion system. Specifically, the acid conversion system may be configured to separate and convert acids into primary, secondary, and/or tertiary alcohols, each of which may be used as alternative fuels or for numerous other applications, including, but not limited to, processes associated with coal-fired generating facilities and industrial process plants. In the acid conversion system, each acid is received individually (i.e., not mixed with other acids or chemicals). Each acid is received in liquid form from an acid separation system (for example, as described above with respect to Example 3) in a separate holding tank (e.g., holding tank 1 (603), holding tank 2 (604), and holding tank 3 (605)).

From holding tank 3 (605), the carbonic acid is directed through fogging pump 3 (617), where the carbonic acid pressure is increased to around 150 psi. From fogging pump 3 (617), the high pressure carbonic acid flows through control valve 3 (608), which modulates the pressure and flow of the carbonic acid to maintain an even distribution of carbonic acid. The high pressure carbonic acid is sent from control valve 3 (608) to hydrolysis chamber 3 (620). The carbonic acid is directed evenly into a first array of high pressure fogging nozzles housed in hydrolysis chamber 3 (620). Simultaneously, a reagent is drawn from reagent storage tank 3 (629) using high pressure pump 3 (626), which increases the pressure of the reagent to around 150 psi. In this Example 4, the reagent is lithium aluminum hydride ($LiAlH_4$). From high pressure pump 3 (626), the high pressure lithium aluminum hydride flows through control valve 6 (623), which modulates the pressure and flow of the lithium aluminum hydride to maintain an even distribution of lithium aluminum hydride. The high pressure lithium aluminum hydride is sent from control valve 6 (623) to hydrolysis chamber 3 (620). The lithium aluminum hydride is directed evenly into a second array of the high pressure fogging nozzles housed in hydrolysis chamber 3 (620).

The first and second array of high pressure fogging nozzles for the carbonic acid and the lithium aluminum hydride are directed against each other so there will be a contact collision of the carbonic acid and the lithium aluminum hydride. The fine carbonic acid and lithium aluminum hydride droplets come in contact with one another at around 150 psi, creating a high burst of energy that causes a hydrolysis reaction. As the hydrolysis reaction is complete, the resulting alcohol drops to the bottom of hydrolysis chamber 3 (620) and is sent to alcohol storage tank 3 (635) via drainage piping (634).

From holding tank 2 (604), the nitric acid is directed through fogging pump 2 (616), where the nitric acid pressure is increased to around 150 psi. From fogging pump 2 (616), the high pressure nitric acid flows through control valve 2 (607), which modulates the pressure and flow of the nitric acid to maintain an even distribution of nitric acid. The high pressure nitric acid is sent from control valve 2 (607) to hydrolysis chamber 2 (619). The nitric acid is directed evenly into a first array of high pressure fogging nozzles housed in hydrolysis chamber 2 (619). Simultaneously, a reagent is drawn from reagent storage tank 2 (628) using high pressure pump 2 (625), which increases the pressure of the reagent to around 150 psi. In this Example 4, the reagent is ROH. From high pressure pump 2 (625), the high pressure reagent flows through control valve 5 (622), which modulates the pressure and flow of the reagent to maintain an even distribution of reagent. The high pressure reagent is sent from control valve 5 (622) to hydrolysis chamber 2 (619). The reagent is directed evenly into a second array of the high pressure fogging nozzles housed in hydrolysis chamber 2 (619).

The first and second array of high pressure fogging nozzles for the nitric acid and the reagent are directed against each other so there will be a contact collision of the nitric acid and the reagent against each another. The fine nitric acid and reagent droplets come in contact with one another at around 150 psi, creating a high burst of energy that causes a hydrolysis reaction. As the hydrolysis reaction is complete, the resulting alcohol (in this example, nitrate ester ($RO-NO_2$)) drops to the bottom of hydrolysis chamber 2 (619) and is sent to alcohol storage tank 2 (633) via drainage piping (632).

From holding tank 1 (603), the sulfuric acid is directed through fogging pump 1 (615), where the nitric acid pressure is increased to around 150 psi. From fogging pump 1 (615), the high pressure sulfuric acid flows through control valve 1 (606), which modulates the pressure and flow of the sulfuric acid to maintain an even distribution of sulfuric acid. The high pressure sulfuric acid is sent from control valve 1 (606) to hydrolysis chamber 1 (618). The sulfuric acid is directed evenly into a first array of high pressure fogging nozzles housed in hydrolysis chamber 1 (618). Simultaneously, a reagent is drawn from reagent storage tank 1 (627) using high pressure pump 1 (624), which increases the pressure of the reagent to around 150 psi. In this Example 4, the reagent is an alkene ($CH_2=CH_2$). From high pressure pump 1 (624), the high pressure reagent flows through control valve 4 (621), which modulates the pressure and flow of the reagent to maintain an even distribution of reagent. The high pressure reagent is sent from control valve 4 (621) to hydrolysis chamber 1 (618). The reagent is directed evenly into a second array of the high pressure fogging nozzles housed in hydrolysis chamber 1 (618).

The first and second array of high pressure fogging nozzles for the sulfuric acid and the reagent are directed against each other so there will be a contact collision of the sulfuric acid and the reagent against each another. The fine sulfuric acid and reagent droplets come in contact with one another at around 150 psi, creating a high burst of energy that causes a hydrolysis reaction. As the hydrolysis reaction is complete, the resulting alcohol (in this example, alkyl hydrogensulphate ($CH_3CH_2OSO_2OH$)) drops to the bottom of hydrolysis chamber 1 (618) and is sent to alcohol storage tank 1 (631) via drainage piping (630).

Applying this invention, in conjunction with the COMPLY 2000 technology, to a 140 MW coal-fired power generation facility, the following results were achieved: 2,245.2 lbs/hr of $SO_X$ (approximately 96% removal), 541.9 lbs/hr of $NO_X$ (approximately 98% removal), and 25,531 lbs/hr of $CO_2$ (approximately 10% removal).

One or more embodiments of the invention eliminate at least ten percent (10%) of the carbon dioxide in the flue gas created from the combustion process. Eliminating carbon dioxide reduces greenhouse gas emissions, improving air quality and, in regulated areas, improving the compliance requirements that a facility may have for carbon dioxide emissions and/or some other emission regulation. One or more embodiments of the invention may enhance energy security by allowing a facility with compliance requirements to run for more hours before exceeding its emission limit.

In one or more embodiments of the invention, primary, secondary, and/or tertiary alcohols are produced. Such alcohols may have a variety of uses, including but not limited to an alternative fuel, an ingredient for a chemical or product, and a catalyst in a process involving chemicals. The creation of alcohol that can be used as a fuel also enhances energy security by allowing ancillary power needed to run the equipment used in the combustion process to run off of the alcohol produced by the process of this invention rather than be purchased externally, possibly from foreign sources.

One or more embodiments of the invention reduce operating costs and increase efficiency by using existing waste heat recovery, such as in the heat exchangers and distillers. One or more embodiments of the invention reduce or eliminate costs associated with neutralizing one or more acids by separating each individual acid from the wastewater stream.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method to convert carbon dioxide ($CO_2$) to a primary alcohol, the method comprising:
    spraying a pressurized water mist into a directional flow of a stream of flue gas comprising the $CO_2$ from a combustion process to create heat and a mixture of liquid carbonic acid ($H_2CO_3$) and wastewater;
    extracting, using the heat, the liquid $H_2CO_3$ from the mixture;
    pressurizing the liquid $H_2CO_3$ extracted from the mixture to generate pressurized liquid $H_2CO_3$;
    combining the pressurized liquid $H_2CO_3$ with a first liquid reagent comprising lithium aluminum hydride ($LiAlH_4$) in a first hydrolysis chamber; and
    creating the primary alcohol from combining the pressurized liquid $H_2CO_3$ with the first liquid reagent comprising $LiAlH_4$.

2. The method of claim 1, further comprising:
    extracting the primary alcohol from the hydrolysis chamber; and
    using the primary alcohol as a fuel to generate power at the facility.

3. The method of claim 1, wherein extracting the liquid $H_2CO_3$ from the mixture comprises:
    receiving the mixture in a trickling filter comprising a media onto which the mixture flows under aerobic conditions resulting in a layer of microbial film to form on the media; and
    removing, using the layer of microbial film, microbial impurities from the mixture.

4. The method of claim 3, wherein extracting the liquid $H_2CO_3$ from the mixture further comprises:
receiving the mixture in a multi-bag filter system comprising a plurality of bags each comprising a pleated cartridge housed in a vessel and configured to remove oils and particles from the mixture.

5. The method of claim 4, wherein extracting the liquid $H_2CO_3$ from the mixture further comprises:
receiving the mixture in a heat exchanger;
heating, using the heat, the mixture in the heat exchanger to between a first and second temperature, wherein the first temperature is a boiling point of the $H_2CO_3$ and wherein the second temperature is a boiling point of the wastewater;
converting liquid $H_2CO_3$ to vapor $H_2CO_3$;
receiving, in a steam separator, the mixture from the heat exchanger;
removing, using the steam separator, the vapor $H_2CO_3$ from the mixture;
receiving, in a distiller, the vapor $H_2CO_3$ from the steam separator; and
removing, using the distiller, the wastewater from the vapor $H_2CO_3$.

6. The method of claim 5, wherein extracting the vapor $H_2CO_3$ from the mixture further comprises:
receiving, using a condenser, the vapor $H_2CO_3$ from the distiller;
cooling the vapor $H_2CO_3$ to a third temperature below the first temperature; and
converting the vapor $H_2CO_3$ to liquid $H_2CO_3$.

7. The method of claim 1, wherein the mixture further comprises liquid sulfuric acid ($H_2SO_4$) and liquid nitric acid ($HNO_3$).

8. The method of claim 7, further comprising:
extracting, along with the liquid $H_2CO_3$, the liquid $H_2SO_4$ and the liquid $HNO_3$ from the mixture;
heating, using a heat exchanger, the liquid $H_2CO_3$, the liquid $H_2SO_4$, and the liquid $HNO_3$;
converting the liquid $H_2CO_3$ to vapor $H_2CO_3$, the liquid $H_2SO_4$ to vapor $H_2SO_4$, and the liquid $HNO_3$ to vapor $HNO_3$;
separating the vapor $H_2CO_3$, the vapor $H_2SO_4$, and the vapor $HNO_3$ in a distiller;
separately condensing each of the vapor $H_2CO_3$, the vapor $H_2SO_4$, and the vapor $HNO_3$ to recreate the liquid $H_2CO_3$, the liquid $H_2SO_4$, and the liquid $HNO_3$, respectively;
separately pressurizing each of the liquid $H_2CO_3$, the liquid $H_2SO_4$, and the liquid $HNO_3$;
combining pressurized liquid $H_2SO_4$ with a second liquid reagent comprising an alkene in a second hydrolysis chamber;
creating a secondary alcohol from combining the pressurized liquid $H_2SO_4$ with the second liquid reagent comprising the alkene;
combining pressurized liquid $HNO_3$ with a third liquid reagent comprising R—O—H (alcohol) in a third hydrolysis chamber; and
creating a tertiary alcohol from combining the pressurized liquid $HNO_3$ with the third liquid reagent comprising the R—O—H (alcohol).

* * * * *